United States Patent
Yamada et al.

(10) Patent No.: US 8,445,652 B2
(45) Date of Patent: May 21, 2013

(54) 3, 6-O-BRIDGED PYRANOSE INVERSION COMPOUND AND PROCESS FOR PRODUCING B-O-PYRANOSIDE

(75) Inventors: Hidetoshi Yamada, Sanda (JP); Noriaki Asakura, Sanda (JP); Yasunori Okada, Sanda (JP)

(73) Assignee: Kwansei Gakuin Educational Foundation, Hyogo (JP)

( * ) Notice: Subject to any disclaimer, the term of this patent is extended or adjusted under 35 U.S.C. 154(b) by 292 days.

(21) Appl. No.: 12/867,582

(22) PCT Filed: Feb. 13, 2009

(86) PCT No.: PCT/JP2009/052416
§ 371 (c)(1),
(2), (4) Date: Aug. 13, 2010

(87) PCT Pub. No.: WO2009/102022
PCT Pub. Date: Aug. 20, 2009

(65) Prior Publication Data
US 2010/0324275 A1 Dec. 23, 2010

(30) Foreign Application Priority Data
Feb. 15, 2008 (JP) .................................. 2008-033960

(51) Int. Cl.
*C07G 3/00* (2006.01)
*C07G 11/00* (2006.01)
*C07H 15/00* (2006.01)
*C07H 17/00* (2006.01)
*C07H 1/00* (2006.01)
*C07H 3/00* (2006.01)
*C07H 15/24* (2006.01)
*C07B 37/00* (2006.01)

(52) U.S. Cl.
USPC ............................ 536/4.1; 536/124; 536/18.1

(58) Field of Classification Search
USPC .......................................... 536/4.1, 124, 18.1
See application file for complete search history.

(56) References Cited

PUBLICATIONS

Yasunori Okada et al., "Highly β-selective O-glucosidation due to the restricted twist-boat conformation," Org. Lett., 9(8), pp. 1573-1576 (2007).
Yasunori Okada. et al., "Highly β-selective and direct formation of 2-O-glycosylated glucosides by ring restriction into twist-boat," Org. Lett., 9(15), pp. 2755-2758 (2007).
Teruaki Mukaiyama et al. "Catalytic and stereoselective glycosylation with disarmed glycosyl fluoride by using a combination of stannous (II) chloride ($SnCl_2$) and silver tetrakis (pentafluorophenyl) borate [$AgB(C_6F_5)_4$] as a catalyst," Chem. Lett., pp. 388-389 (2001).
Yasunori Okada et al., "Highly β-selective O-glucosidation by means of an axial-rich glucosyl donor due to 3,6-O-(o-xylylene) group," Preprints of 88th Annual Meeting on Chemical Society of Japan in Spring 2008 Koen Yokoshu II, p. 1012 (yoko No. 2 G2-15) (2008).
Noriaki Asakura et al., "β-selective O-glucosidation using 3,6-O-(o-xylylene)-bridged glucosyl fluoride," Preprints of 88th Annual Meeting on Chemical Society of Japan in Spring 2008 Koen Yokoshu II, p. 1012 (yoko No. 2 G2-17)(2008).
Kerry Routenberg Love et al., "Linear synthesis of a protected H-type II pentasaccharide using glycosyl phosphate building blocks," J. Org. Chem, 66, pp. 8165-8176 (2001).
Geert-Jan Boons, "Recent developments in chemical oligosaccharide synthesis," Contemp. Organic Syn., 3, pp. 173-200 (1996).
Horst Kunz et al., "Glycosidsynthese mit 2,3,4,6-tetra-O-pivaloyl-α-D-glucopyranosylbromid," Liebigs Ann. Chem., pp. 41-48 (1982).
Garegg et al., "Observations on silver trifluoromethane sulfonate-promoted syntheses of 1,2-*trans*-glycosides from acylated glycosyl bromides," Acta. Chem. Scand. B, 33, pp. 116-118 (1979).
Koenigs et al. "Ueber einige derivate des traubenzuckers und der galactose," E. Chem. Ber., pp. 957-981 (1901).

*Primary Examiner* — Scarlett Goon
(74) *Attorney, Agent, or Firm* — Wenderoth, Lind & Ponack, L.L.P.

(57) ABSTRACT

An object of the present invention is to provide a 3,6-O-bridged pyranose-inverted compound useful for being easy to produce β-O-pyranosides selectively.

The 3,6-O-bridged pyranose-inverted compound according to the present invention is represented by General Formula (1):

[Chem. 1]

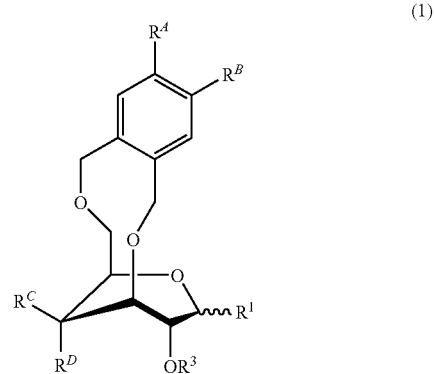

(1)

wherein $R^A$ and $R^B$ each represent hydrogen or are bonded to each other to form a benzene ring; one of $R^C$ and $R^D$ represents hydrogen and the other represents $—OR^2$; $R^1$ represents hydroxy or halogen; and $R^2$ and $R^3$ each represent a hydroxy-protecting group.

10 Claims, No Drawings

3,6-O-BRIDGED PYRANOSE INVERSION COMPOUND AND PROCESS FOR PRODUCING B-O-PYRANOSIDE

TECHNICAL FIELD

The present invention relates to a 3,6-O-bridged pyranose-inverted compound and a process for producing β-O-pyranoside.

BACKGROUND ART

Pyranoside is a compound that results from the glycosylation of pyranose (sugar) with an alcohol such as a naturally occurring steroid. Pyranoside has two isomers: α-O-pyranoside and β-O-pyranoside. Among them, β-O-pyranoside is an important compound having various bioactivities.

General chemical synthesis to produce pyranoside provides a mixture of α-O-pyranoside and β-O-pyranoside; therefore, it is impossible to produce β-O-pyranoside selectively by such chemical synthesis.

It is, however, possible to produce β-O-pyranoside selectively by applying neighboring group participation using a sugar donor in which the 2-position of the sugar is protected with an acyl group (Non-Patent Literatures 1 to 5). However, this method has a drawback such that the electron withdrawing property of the acyl group decreases the glycosylation speed. Moreover, this method cannot be applied when the acyl group cannot be introduced into the 2-position of the sugar.

Accordingly, there has been a demand for development of a new method which enables selective β-expression without applying the neighboring group participation, particularly, the development of a process for easily producing a corresponding β-O-pyranoside at a high selectivity and a high yield without requiring strict reaction conditions, even when various alcohols are used in the reaction; and a demand for development of a new pyranose donor (β-O-glycosylating agent) to be used in such a process.

[Non-patent Literature 1]
Love, K. R., Andrade, R. B., Seeberger, H. P. J. Org. Chem., 2001, 66, pp. 8165-8176
[Non-patent Literature 2]
Boons, G. J. Contemp. Org. Synth., 1996, 3, pp. 173-200
[Non-patent Literature 3]
Kunz, H., Harreus, A. Liebigs Ann. Chem., 1982, pp. 41-48
[Non-patent Literature 4]
Garegg. J. P., Norberg, T. Acta. Chem. Scand. B., 1979, 33, pp. 116-118
[Non-patent Literature 5]
Koenigs. W., Knorr, E. Chem. Ber., 1901, pp. 957-981

DISCLOSURE OF THE INVENTION

[Technical Problem]

An object of the present invention is to provide a process for easily producing β-O-pyranoside at a high selectivity without requiring strict reaction conditions, and to provide a pyranose donor to be used in the process.

[Technical Solution]

The inventors of the present invention conducted extensive research to solve the foregoing problems and succeeded in synthesizing a 3,6-O-bridged pyranose-inverted compound represented by the following General Formula (1). The inventors found that the 3,6-O-bridged pyranose-inverted compound can serve as the desired β-O-glycosylating agent. The present invention has been completed based on this finding.

The present invention provides 3,6-O-bridged pyranose-inverted compounds according to the following Items 1 to 5, and a process for producing β-O-pyranoside according to Item 6.

Item 1. A 3,6-O-bridged pyranose-inverted compound, represented by General Formula (1):

[Chem. 1]

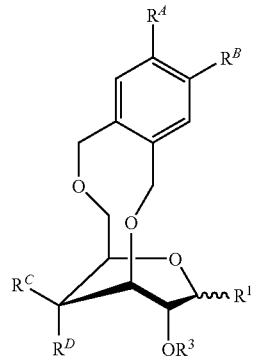

(1)

wherein $R^A$ and $R^B$ each represent hydrogen or are bonded to each other to form a benzene ring; one of $R^C$ and $R^D$ represents hydrogen and the other represents $-OR^2$; $R^1$ represents hydroxy or halogen; and $R^2$ and $R^3$ each represent a hydroxy-protecting group.

Item 2. The 3,6-O-bridged pyranose-inverted compound according to Item 1, wherein $R^A$ and $R^B$ each represent hydrogen; $R^C$ represents hydrogen; and $R^D$ represents $-OR^2$.

Item 3. The 3,6-O-bridged pyranose-inverted compound according to Item 1, wherein $R^A$ and $R^B$ each represent hydrogen; $R^C$ represents $-OR^2$; and $R^D$ represents hydrogen.

Item 4. The 3,6-O-bridged pyranose-inverted compound according to Item 1, wherein $R^A$ and $R^B$ are bonded to each other to form a benzene ring; $R^C$ represents hydrogen; and $R^D$ represents $-OR^2$.

Item 5. The 3,6-O-bridged pyranose-inverted compound according to Item 1, wherein the hydroxy-protecting group represented by $R^2$ and $R^3$ is benzyl, dimethyl benzyl, 4-methoxybenzyl, allyl or trialkyl silyl.

Item 6. A process for producing β-O-pyranoside represented by General Formula (3):

[Chem. 3]

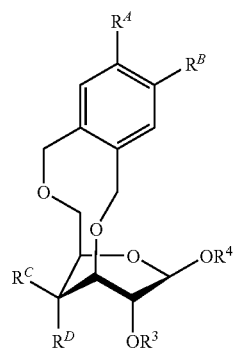

(3)

wherein $R^A$ and $R^B$ each represent hydrogen or are bonded to each other to form a benzene ring; one of $R^C$ and $R^D$ represents hydrogen and the other represents $-OR^2$; $R^2$ and $R^3$ each represent a hydroxy-protecting group; and $R^4$ represents a residue of a primary, secondary or tertiary alcohol, the process comprising reacting a 3,6-O-bridged pyranose-inverted compound represented by General Formula (1B):

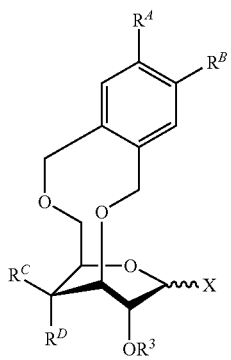

(1B)

wherein X represents halogen; and $R^A$, $R^B$, $R^C$, $R^D$, $R^2$ and $R^3$ are the same as above, with an alcohol represented by General Formula (2):

$R^4OH$ wherein $R^4$ is the same as above.

3,6-O-Bridged Pyranose-inverted Compound

The 3,6-O-bridged pyranose-inverted compound of the present invention is represented by the following General Formula (1).

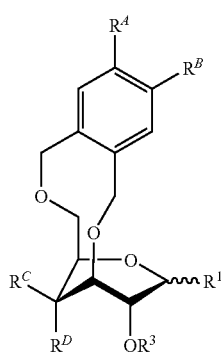

(1)

wherein $R^A$, $R^B$, $R^C$, $R^D$, $R^1$ and $R^3$ are the same as above.

Examples of the halogen represented by $R^1$ include fluorine, chlorine, bromine, and iodine.

Examples of the hydroxy protecting groups represented by $R^2$ and $R^3$ include benzyl, dimethyl benzyl, 4-methoxybenzyl, allyl, and trialkyl silyl.

Examples of the 3,6-O-bridged pyranose-inverted compounds represented by General Formula (1) include the compounds represented by the following General Formulas (1A) and (1B).

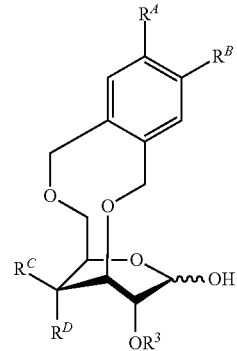

(1A)

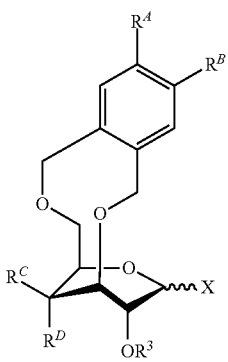

(1B)

wherein $R^A$, $R^B$, $R^C$, $R^D$, $R^3$ and X are the same as above.

In addition, among the 3,6-O-bridged pyranose-inverted compounds represented by General Formula (1), the compounds represented by the following General Formulas (1a), (1b) and (1c) are preferable.

[Chem.6]

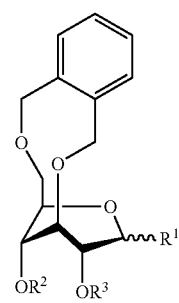

(1a)

-continued

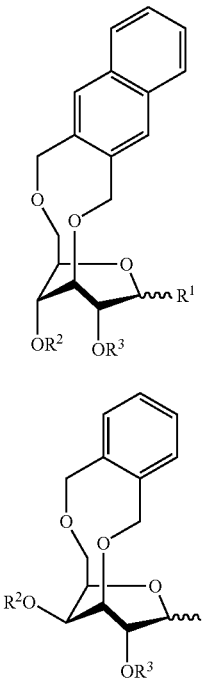

(1b)

(1c)

wherein $R^1$, $R^2$ and $R^3$ are the same as above.

The 3,6-O-bridged pyranose-inverted compound of the present invention represented by General Formula (1a) is produced, for example, in the manner shown by Reaction Scheme-1.

Reaction scheme - 1

[Chem. 7]

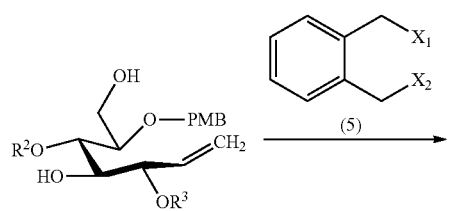

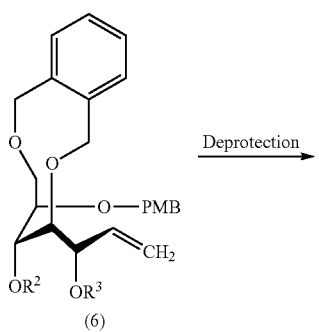

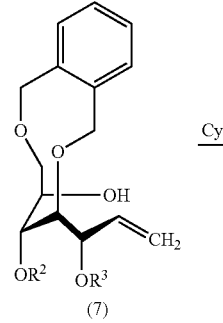

(7)

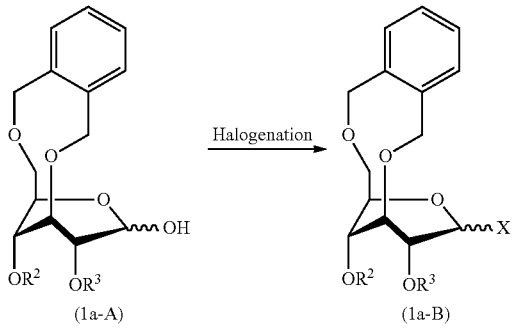

(1a-A)       (1a-B)

wherein $R^2$, $R^3$ and X are the same as above, PMB represents 4-methoxybenzyl, and $X_1$ and $X_2$ each represent halogen.

The 3,6-O-bridged pyranose-inverted compound of the present invention, wherein $R^1$ represents hydroxy (the compound represented by General Formula (1a-A)), is produced by reacting the compound represented by General Formula (4) with the compound represented by General Formula (5), deprotecting the resulting reaction product, which is the compound represented by General Formula (6), and further cyclizing the compound represented by General Formula (7), which resulted from the deprotection.

The 3,6-O-bridged pyranose-inverted compound of the present invention, wherein $R^1$ represents halogen (the compound represented by General Formula (1a-B)), is produced by halogenating the compound represented by General Formula (1a-A) obtained above.

As shown in Example 1 described later, the reaction between the compound of General Formula (4) and the compound of General Formula (5) is performed, for example, in a solvent such as dimethylformamide in the presence of a basic compound such as sodium hydride. This reaction is preferably performed under stirring, at first for 5 to 30 minutes at room temperature, and then for another 30 minutes to 3 hours at an increased reaction temperature of about 100° C. The compound of General Formula (4) and the compound of General Formula (5), which are used as starting materials of the reaction, are both known compounds that can be easily obtained, or compounds that can be easily produced from known compounds.

As shown in Example 2 described later, the deprotection of the compound of General Formula (6) is performed, for example, in a solvent such as dichloromethane in the presence of an oxidant such as 2,3-dichloro-5,6-dicyano-1,4-benzoquinone. The reaction is preferably performed using a phosphate buffer solution so as to keep the pH value in the reaction system around 7.4. The reaction is performed under stirring for about 1 to 2 hours at a temperature around 0° C.

As shown in Example 3 described later, the cyclization of the compound (7) is performed, for example, in a solvent such as acetone-water, etc., under stirring in the presence of 4-methylmorpholine-N-oxide and osmium tetraoxide for about 1 to 3 hours at around room temperature. After that, sodium periodate is added and stirring is continued for about 3 to 7 hours at around room temperature.

As shown in Example 4 described later, the halogenation of the compound of General Formula (1a-A) is performed, for example, in a solvent such as tetrahydrofuran under stirring in the presence of (dimethylamino)sulfur trifluoride for about 20 minutes to 1 hour at around 0° C. to room temperature.

The 3,6-O-bridged pyranose-inverted compound of the present invention represented by General Formula (1a) may also be produced in the method represented by Reaction Scheme-2. The method of Reaction Scheme-2 eases purification in each reaction step, allowing the object compound to be produced at a high yield.

Reaction scheme - 2

[Chem. 8]

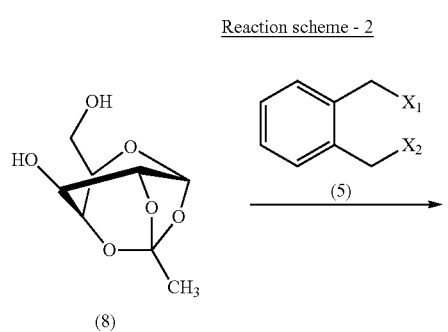

(8)

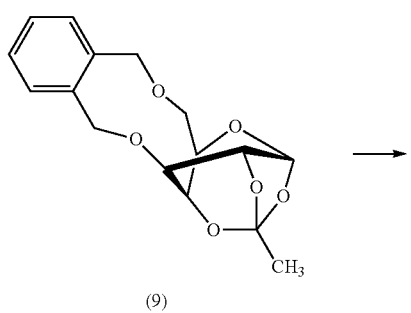

(9)

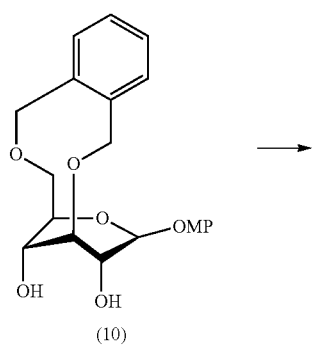

(10)

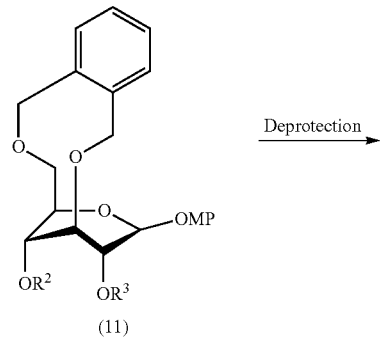

(11)

Deprotection

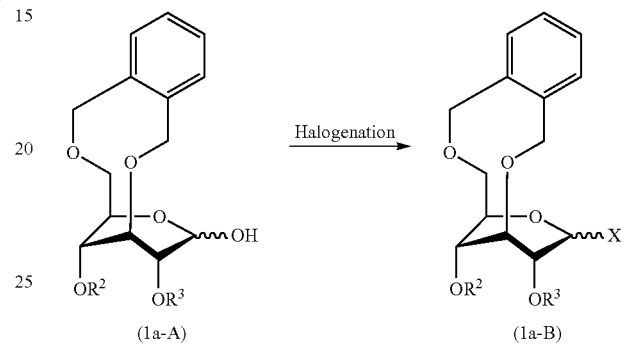

(1a-A)  Halogenation  (1a-B)

wherein $R^2$, $R^3$, X, $X_1$ and $X_2$ are the same as above, and MP represents 4-methoxyphenyl.

As shown in Example 5 described later, the reaction between the compound (8) with the compound (5) is performed, for example, in a solvent such as dimethylformamide in the presence of a basic compound such as sodium hydride. This reaction is preferably performed under stirring for 2 to 3 hours at about 70° C. to the boiling point of the solvent. The compound (8) used as a starting material of the reaction is a known compound. Reaction Scheme-5 shown later represents an industrially favorable method for producing the compound (8).

As shown in Example 6 described later, the reaction that produces the compound (10) from the compound (9) is performed, for example, by reacting 4-methoxyphenol with the compound (9) without a solvent. The reaction mixture is then treated with a molecular sieve in a solvent such as methanol for about 3 to 8 hours at 50° C. to 70° C.

As shown in Example 7 described later, the reaction that produces the compound (11) from the compound (10) is performed, for example, in a solvent such as dimethylformamide in the presence of a basic compound such as sodium hydride. The reaction is performed for about 3 to 7 hours at about 70° C. to 90° C.

As shown in Example 8 described later, the deprotection of the compound (11) is performed, for example, in a solvent such as acetonitrile, water, etc., in the presence of cerium sulfate for about 10 to 20 hours at room temperature.

The halogenation of the compound (1a-A) is performed in the same manner as that represented by Reaction Scheme-1.

The 3,6-O-bridged pyranose-inverted compound of the present invention represented by General Formula (1b) is produced, for example, according to the method represented by Reaction Scheme-3.

Reaction scheme - 3

[Chem. 9]

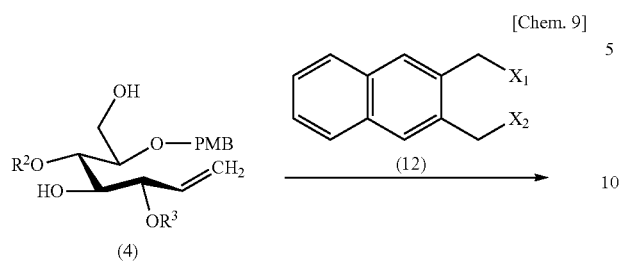

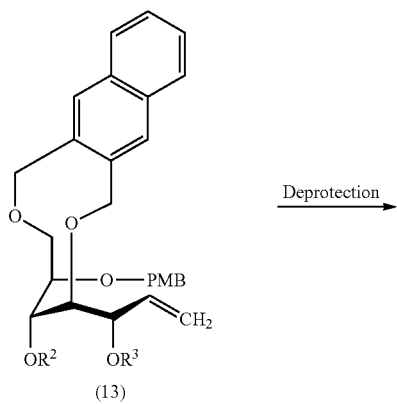

Deprotection

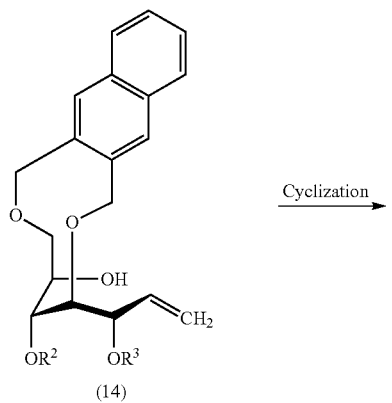

Cyclization

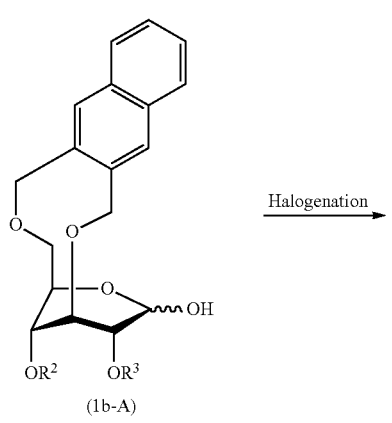

Halogenation

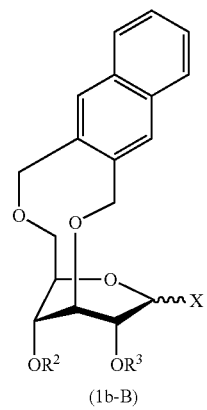

wherein $R^2$, $R^3$, X, PMB, $X_1$ and $X_2$ are the same as above.

As shown in Example 9 described later, the reaction between the compound (4) and the compound (12) is performed, for example, in a solvent such as dimethylformamide or toluene in the presence of a basic compound such as sodium hydride. This reaction is preferably performed for about 1 to 3 hours at about 50° C. to 70° C. The compound (4) and the compound (12), which are used as starting materials of the reaction, are both known compounds that can be easily obtained.

As shown in Example 10 described later, the deprotection of the compound (13) is performed, for example, in a solvent such as acetonitrile in the presence of zirconium chloride (IV). This reaction is performed for about 10 to 30 minutes at about room temperature.

As shown in Example 11 described later, the cyclization of the compound (14) is performed, for example, in a solvent such as acetone, water, etc., in the presence of 4-methylmorpholine-N-oxide and osmium tetraoxide for about 3 to 6 hours at around room temperature. After that, the reaction is continued in the presence of an oxidant such as sodium periodate for about 30 to 60 minutes at around room temperature.

The halogenation of the compound (1b-A) is performed under the same conditions as those for the halogenation of the compound (1a-A) according to the method of Reaction Scheme-1.

The 3,6-O-bridged pyranose-inverted compound of the present invention represented by General Formula (1c) is produced, for example, according to the method represented by Reaction Scheme-4.

Reaction scheme - 4

[Chem. 10]

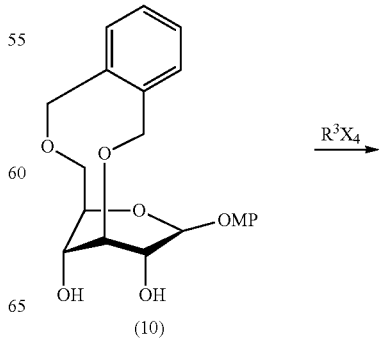

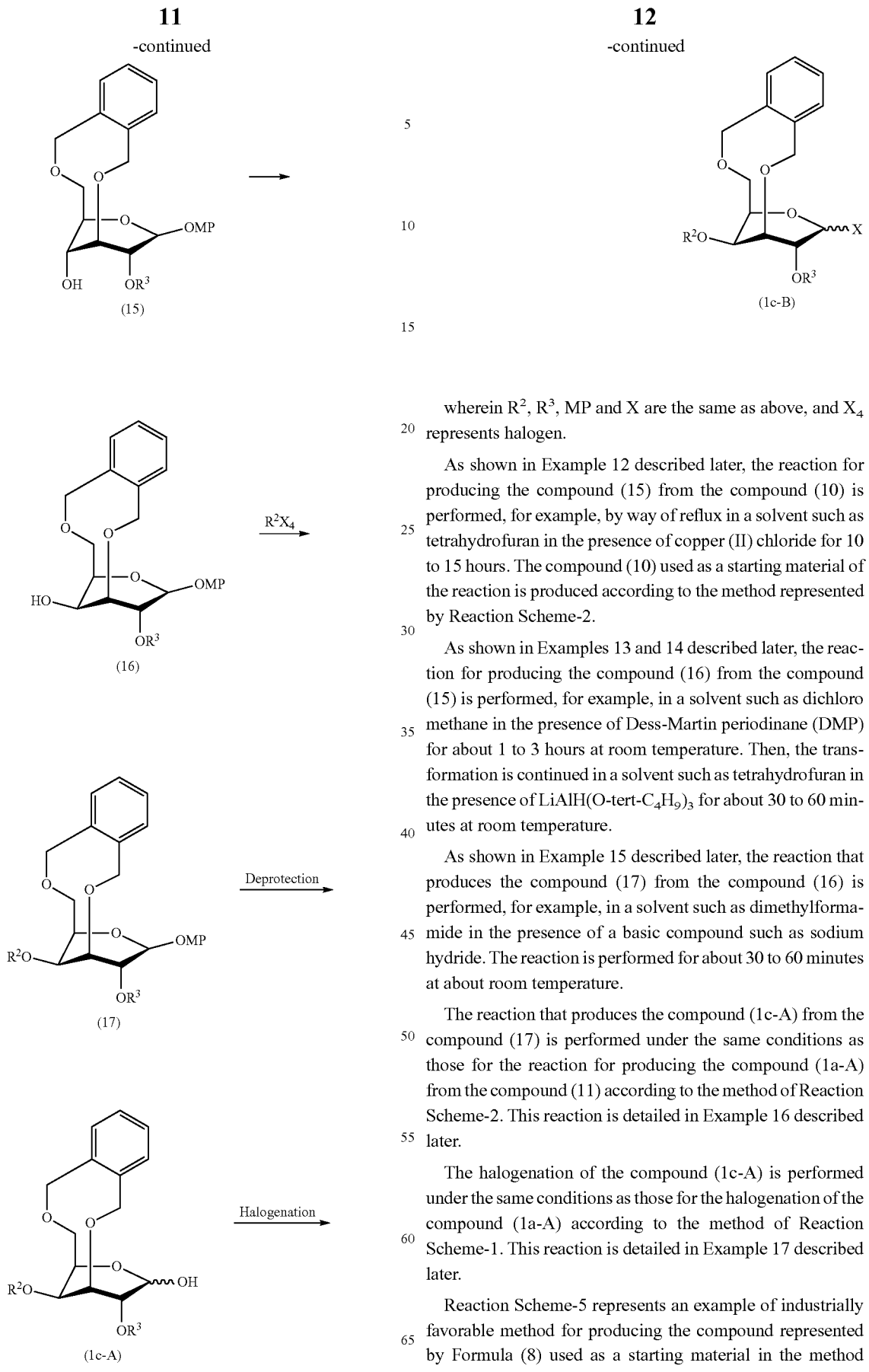

wherein $R^2$, $R^3$, MP and X are the same as above, and $X_4$ represents halogen.

As shown in Example 12 described later, the reaction for producing the compound (15) from the compound (10) is performed, for example, by way of reflux in a solvent such as tetrahydrofuran in the presence of copper (II) chloride for 10 to 15 hours. The compound (10) used as a starting material of the reaction is produced according to the method represented by Reaction Scheme-2.

As shown in Examples 13 and 14 described later, the reaction for producing the compound (16) from the compound (15) is performed, for example, in a solvent such as dichloro methane in the presence of Dess-Martin periodinane (DMP) for about 1 to 3 hours at room temperature. Then, the transformation is continued in a solvent such as tetrahydrofuran in the presence of $LiAlH(O\text{-tert-}C_4H_9)_3$ for about 30 to 60 minutes at room temperature.

As shown in Example 15 described later, the reaction that produces the compound (17) from the compound (16) is performed, for example, in a solvent such as dimethylformamide in the presence of a basic compound such as sodium hydride. The reaction is performed for about 30 to 60 minutes at about room temperature.

The reaction that produces the compound (1c-A) from the compound (17) is performed under the same conditions as those for the reaction for producing the compound (1a-A) from the compound (11) according to the method of Reaction Scheme-2. This reaction is detailed in Example 16 described later.

The halogenation of the compound (1c-A) is performed under the same conditions as those for the halogenation of the compound (1a-A) according to the method of Reaction Scheme-1. This reaction is detailed in Example 17 described later.

Reaction Scheme-5 represents an example of industrially favorable method for producing the compound represented by Formula (8) used as a starting material in the method represented by Reaction Scheme-2.

Reaction scheme - 5

[Chem. 11]

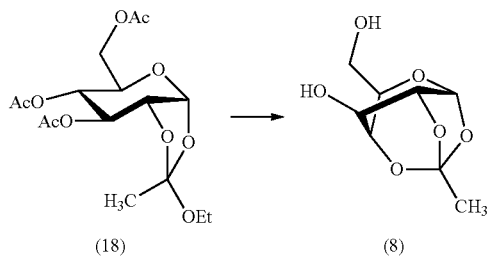

(18) → (8)

wherein Ac represents acetyl and Et represents ethyl.

As shown in Example 18 described later, the reaction that produces the compound (8) from the compound (18) is performed, for example, by treating the compound (18) in a solvent such as methanol in the presence of a basic compound such as DBU, followed by reflux in a solvent such as dichloroethane in the presence of p-toluene sulfonic acid for 5 to 8 hours.

Separation and purification of the object compounds obtained through the methods represented by Reaction Scheme-1, Reaction Scheme-2, Reaction Scheme-3, Reaction Scheme-4 and Reaction Scheme-5 from the reaction mixtures are performed using usual means. Separation and purification are performed, for example, by way of evaporation, recrystallization, column chromatography, ion-exchange chromatography, gel chromatography, affinity chromatography, preparative thin-layer chromatography, solvent extraction, or the like.

The 3,6-O-bridged pyranose-inverted compound of the present invention represented by General Formula (1B) is useful as a β-O-glycosylating agent.

The 3,6-O-bridged pyranose-inverted compound of the present invention represented by General Formula (1A) is useful as an intermediate for producing a 3,6-O-bridged pyranose-inverted compound represented by General Formula (1B), which is useful as a β-O-glycosylating agent.

Process for Producing β-O-pyranoside

By reacting the 3,6-O-bridged pyranose-inverted compound represented by General Formula (1B) with the alcohol represented by General Formula (2), it is possible to selectively synthesize only the β-O-pyranoside represented by General Formula (3) (Reaction Scheme-6).

Reaction scheme - 6

[Chem. 12]

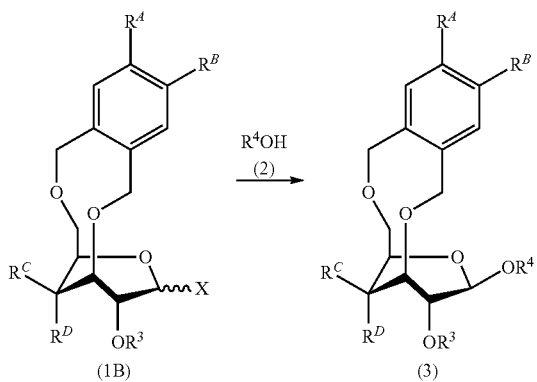

(1B) → (3)

wherein $R^A$, $R^B$, $R^C$, $R^D$, $R^3$, $R^4$ and X are the same as above.

The residue of a primary, secondary or tertiary alcohol represented by $R^4$ in General Formula (2) is a residue resulting from the removal of hydroxy from a primary, secondary or tertiary alcohol.

The alcohol represented by General Formula (2) is a known compound, which includes the following alcohols. In the following formulas, Bn represents benzyl, and Me represents methyl.

[Chem. 13]

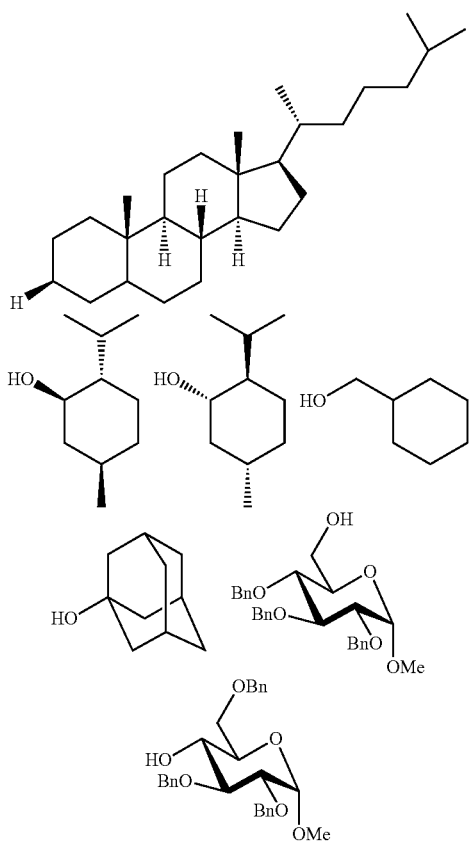

The reaction between the compound represented by General Formula (1B) with the alcohol represented by General Formula (2) is performed in a suitable solvent, for example, a fluorous solvent, such as benzotrifluoride; an aromatic hydrocarbon solvent such as benzene, toluene, or xylene; an ether solvent such as diethylether or dioxane; or a halogenated hydrocarbon solvent such as methylene chloride, chloroform, or carbon tetrachloride. These solvents are preferably anhydrous solvents.

The ratio of the compound represented by General Formula (1B) to the alcohol represented by General Formula (2) is preferably adjusted such that about 0.5 to 2 mol, more preferably about 0.7 to 1.5 mol, of the alcohol is used per mol of the compound represented by General Formula (1B).

The reaction between the compound represented by General Formula (1B) and the alcohol represented by General Formula (2) is preferably performed in a reaction system containing an activator. A suitable activator is, for example, $SnCl_2/AgB(C_6F_5)_4$. The amount of the activator is, for $SnCl_2$, generally about 0.1 to 0.3 mol, preferably about 0.2 mol, per mol of the compound represented by General Formula (1B). For AgB(C$_6$F$_5$)$_4$, the amount is generally about 0.1 to 0.3 mol, preferably about 0.2 mol, per mol of the compound represented by General Formula (1B).

By using a molecular sieve (e.g., molecular sieve 5A) in the reaction, the yield of the object compound becomes higher.

The reaction generally proceeds at about 10° C. to 30° C., preferably at about room temperature. The reaction is usually completed in 1 to 3 hours.

The β-O-pyranoside resulting from the above reaction is separated from the reaction mixture using a general separation means, and is then purified. The separation and purification are performed, for example, by way of evaporation, recrystallization, column chromatography, ion-exchange chromatography, gel chromatography, affinity chromatography, preparative thin-layer chromatography, solvent extraction, or the like.

The various β-O-pyranosides obtained through the above reactions are useful for various important purposes such as the synthesis of sugars, synthesis of terpene glycosides, or the like.

EFFECT OF THE INVENTION

The 3,6-O-bridged pyranose-inverted compound of the present invention represented by General Formula (1) is useful as a β-O-glycosylating agent.

The 3,6-O-bridged pyranose-inverted compound of the present invention represented by General Formula (1) enables easy production of β-O-pyranosides with high selectivity without requiring strict reaction conditions.

BEST MODE FOR CARRYING OUT THE INVENTION

The following more specifically describes the present invention while making reference to examples.

EXAMPLE 1

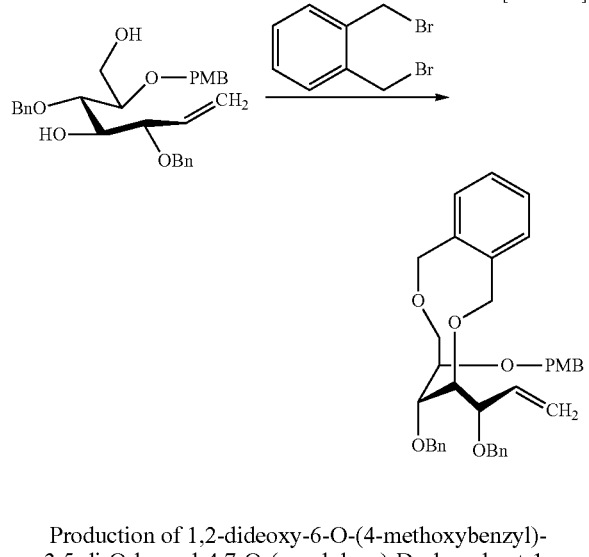

[Chem. 14]

Production of 1,2-dideoxy-6-O-(4-methoxybenzyl)-3,5-di-O-benzyl-4,7-O-(o-xylylene)-D-gluco-hept-1-enitol A benzene solution of 1,2-dideoxy-6-O-(4-methoxybenzyl)-3,5-di-O-benzyl-D-gluco-hept-1-enitol (5.74 g, 12.0 mmol) was concentrated to remove a trace amount of moisture contained in the starting material. Dimethylformamide (600 ml) and 60% NaH in mineral oil (1.92 g; 1.15 g as NaH, 48.0 mmol) were added to the residue, and the mixture was stirred for 15 minutes at room temperature. Subsequently, α,α'-dibromoxylene (9.5 g, 36.0 mmol) was added to the mixture, followed by stirring for 10 minutes at room temperature, and further stirring for 1 hour at 100° C. After cooling the reaction mixture to room temperature, aqueous saturated ammonium chloride solution (50 ml) and water (600 ml) were subsequently added to quench the reaction. The resulting mixture was extracted with ethyl acetate (1 liter×1, 500 ml×1). The combined extract was successively washed with water (500 ml×1) and a saline solution (500 ml×1), dried over magnesium sulfate, and filtered. After the filtrate was concentrated, the resulting residue was purified by middle pressure silica gel chromatography (180 g of SiO$_2$, n-hexane/ethyl acetate=15/1→6/1 gradient) to afford the object compound (3.53 g, yield=51%) as yellow oil. The oily product was allowed to stand at room temperature, and it turned into a pale yellow solid.

The following are the physico-chemical properties of the object compound.

mp: 95° C. to 97° C.

$[\alpha]^D_{24}$=−28.3° (c=2.35, CHCl$_3$)

IR (ZnSe): 3063, 3030, 2934, 2888, 1512, 1248, 1078, 735 cm$^{-1}$ $^1$H-NMR (400 MHz, CDCl$_3$): δ ppm 7.42-7.21 (m, 13H), 4.15 (br d, J=8.7 Hz, 3H), 6.83 (ddd, J=8.7, 3.0, 2.0 Hz, 2H), 5.49 (ddd. J=17.0, 10.5, 7.6 Hz, 1H), 5.17 (br dd, J=10.5, 1.8 Hz, 1H), 5.14 (br dd, J=17.0, 1.1 Hz, 1H), 5.08 (d, J=11.7 Hz, 1H), 4.78 (d, J=11.7 Hz, 1H), 4.77 (d, J=12.4 Hz, 1H), 4.73 (d, J=11.7 Hz, 1H), 4.67 (d, J=12.4 Hz, 1H), 4.59 (d, J=11.5 Hz, 1H), 4.58 (d, J=11.7 Hz, 1H), 4.57 (dd, J=12.8, 3.0 Hz, 1H), 4.46 (d, J=11.5 Hz, 1H), 4.36 (d, J=11.7 Hz, 1H), 4.22 (d, J=11.7 Hz, 1H), 4.19 (dd, J=7.7, 7.6 Hz, 1H), 3.92 (dd, J=12.8, 3.9 Hz, 1H), 3.80 (s, 3H), 3.60 (br d, J=1.4 Hz, 1H), 3.36 (dd, J=8.5, 1.8 Hz, 1H), 3.27 (br dd, J=3.4, 3.4 Hz, 1H)

$^{13}$C-NMR (100 MHz, CDCl$_3$): δ ppm 159.2 (s, 1C), 139.4 (s, 1C), 139.0 (s, 1C), 138.7 (s, 1C), 136.6 (s, 1C), 135.1 (d, 1C), 131.6 (d, 1C), 131.5 (d, 1C), 129.2 (d, 2C), 129.1 (d, 2C), 128.5 (d, 2C), 128.3 (d, 2C), 127.8 (d, 2C), 127.6 (d, 2C), 119.5 (t, 1C), 113.9 (d, 2C), 83.8 (d, 1C), 83.2 (d, 1C), 81.9 (d, 1C), 78.9 (d, 1C), 73.6 (t, 1C), 73.4 (t, 1C), 73.3 (t, 1C), 71.9 (t, 1C), 71.2 (t, 1C), 71.2 (t, C)

HRMS-ESI (m/z): [M+Na]$^+$

Calcd for C$_{37}$H$_{40}$O$_6$, 603.2723; found 603.2720.

EXAMPLE 2

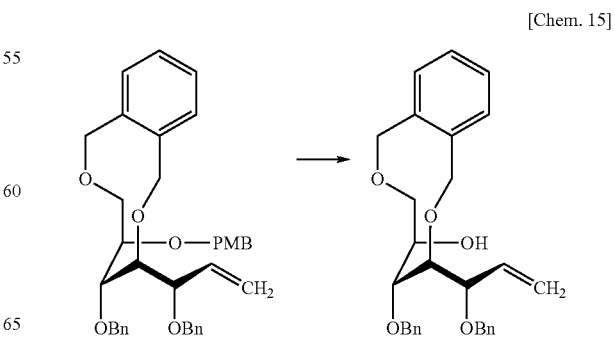

[Chem. 15]

Production of 1,2-dideoxy-3,5-di-O-benzyl-4,7-O-(o-xylylene)-D-gluco-hept-1-enitol A mixture of a dichloromethane (4.0 ml) solution of the 1,2-dideoxy-6-O-(4-methoxybenzyl)-3,5-di-O-benzyl-4,7-O-(o-xylylene)-D-gluco-hept-1-enitol (250 mg, 0.430 mmol) obtained in Example 1 and a phosphate buffer solution (pH value=7.41, 0.8 ml) was stirred at 0° C. Then, 2,3-dichloro-5,6-dicyano-1,4-benzoquinone (117 mg, 0.510 mmol) was added to the mixture. After stirring the mixture for 1.5 hours at the same temperature, the reaction was quenched by the addition of a 10% sodium thiosulfate aqueous solution (20 ml), and the aqueous layer was separated. The organic layer was successively washed with aqueous saturated sodium bicarbonate solution (20 ml×1), water (20 ml×1), and a saline solution (20 ml×1), followed by drying over magnesium sulfate and filtration. After the filtrate was concentrated, the resulting residue was purified by silica gel column chromatography (7.5 g of $SiO_2$, n-hexane/ethyl acetate=4/1→3/1→2/1) to afford the object compound (168 mg, yield=85%) as a white solid.

The following are the physico-chemical properties of the object compound.

mp: 97° C. to 98° C.

$[\alpha]_D^{24}$=−3.24° (c=1.02, $CHCl_3$)

IR (ZnSe): 3425, 3063, 3030, 2886, 1084 $cm^{-1}$ $^1$H-NMR (400 MHz, $CDCl_3$): δ ppm 7.42-7.33 (m, 4H), 7.31-7.20 (m, 10H), 5.76 (ddd, J=17.4, 10.5, 7.8 Hz, 1H), 5.33 (ddd, J=10.5, 1.6, 0.4 Hz, 1H), 5.28 (ddd, J=17.4, 1.6, 0.7 Hz, 1H), 4.99 (d, J=13.3 Hz, 1H), 4.96 (d, J=10.8 Hz, 1H), 4.76 (d, J=10.8 Hz, 1H), 4.65 (d, J=11.6 Hz, 1H), 4.60 (d, J=11.6 Hz, 1H), 4.52 (d, J=13.3 Hz, 1H), 4.50 (d, J=12.0 Hz, 1H), 4.47 (d, J=12.0 Hz, 1H), 4.23 (dd, J=7.8, 7.6 Hz, 1H), 4.03 (dd, J=10.8, 6.2 Hz, 1H), 3.87 (dd, J=7.6, 2.8 Hz, 1H), 3.81 (ddd, J=6.2, 3.0, 2.8 Hz, 1H), 3.69 (dd, J=6.2, 3.2 Hz, 1H), 3.68 (dd, J=7.6, 3.0 Hz, 1H)

$^{13}$C-NMR (100 MHz, $CDCl_3$): δ ppm 138.6 (s, 2C), 128.3 (s, 1C), 136.9 (s, 1C), 135.4 (d, 1C), 131.2 (d, 1C), 129.7 (d, 1C), 128.8 (d, 1C), 128.6 (d, 2C), 128.5 (d, 2C), 128.2 (d, 1C), 128.0 (d, 4C), 127.8 (d, 1C), 127.7 (d, 1C), 119.9 (t, 1C), 83.8 (d, 1C), 82.8 (d, 1C), 78.7 (d, 1C), 75.0 (t, 1C), 73.6 (t, 1C), 73.1 (t, 1C), 73.0 (t, 1C), 72.8 (d, 1C), 71.0 (t, 1C)

HRMS-ESI (m/z): $[M+Na]^+$

Calcd for $C_{29}H_{32}O_5$, 483.2147; found 483.2145.

EXAMPLE 3

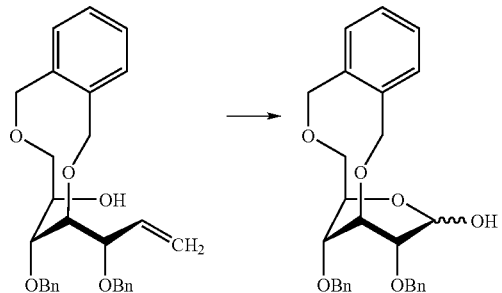

[Chem. 16]

Production of 2,4-di-O-benzyl-3,6-O-(o-xylylene)-D-glucopyranose

An aqueous solution of osmium tetraoxide (25 mg/ml solution in distilled water, 2.00 ml, 0.197 mmol) was added to a mixture obtained by mixing the 1,2-dideoxy-3,5-di-O-benzyl-4,7-O-(o-xylylene)-D-gluco-hept-1-enitol (598 mg, 1.30 mmol) obtained in Example 2 and 4-methyl morpholine N-oxide (608 g, 5.19 mmol) in acetone (10 ml) under stirring. After stirring the mixture for 2 hours at room temperature, sodium periodate (695 mg, 3.25 mmol) and distilled water (2 ml) were added, followed by further stirring for 5 hours at room temperature. The mixture was filtered through Celite, and concentrated. The residue was diluted with ethyl acetate (40 ml), successively washed with a 10% sodium thiosulfate aqueous solution (15 ml×1), water (10 ml) and a saline solution (10 ml×1), dried over magnesium sulfate and filtered. The filtrate was concentrated to afford the object compound as a white solid. The residue was used for the next reaction without being purified.

The following are the physico-chemical properties of the object compound.

mp: 117° C. to 119° C.

$[\alpha]_D^{25}$=+97.5° (c=0.64, $CHCl_3$)

IR (ZnSe): 3409, 3029, 2903, 2870, 1455, 1115, 1028, 752, 698 $cm^{-1}$ $^1$H-NMR (400 MHz, $CDCl_3$): δ ppm 7.39-7.10 (m, 14H; Ar—H), 5.51 (d, J=9.6 Hz, 1H; $CHHC_6H_4$), 5.08 (d, J=10.1 Hz, 1H; $CHHC_6H_4$), 5.02 (dd, J=6.6, 6.4 Hz, 1H; H-1), 4.78 (d, J=12.2 Hz, 1H; $CHHC_6H_4$), 4.68 (d, J=12.2 Hz, 1H; $CHHC_6H_4$), 4.65 (d, J=11.9 Hz, 1H; $CHHC_6H_4$), 4.51 (d, J=11.9 Hz, 1H; CHHPh), 4.38 (br s, 1H; H-3), 4.32 (d, J=10.1 Hz, 1H; $CHHC_6H_4$), 4.30 (d, J=9.6 Hz, 1H; $CHHC_6H_4$), 4.15 (d, J=3.4 Hz, 1H; H-5), 3.94 (d, J=3.0 Hz, 1H; H-4), 3.81 (d, J=13.8 Hz, 1H; H-6), 3.75 (dd, J=13.8, 3.4 Hz, 1H; H-6), 3.57 (d, J=6.4 Hz, 1H; H-2), 3.29 (d, J=6.6 Hz, 1H; OH)

$^{13}$C-NMR (100 MHz, $CDCl_3$): δ ppm 138.6 (s, 1C), 138.0 (s, 1C), 137.1 (s, 1C), 136.6 (s, 1C), 129.8 (d, 1C), 128.8 (d, 1C), 128.6 (d, 2C), 128.5 (d, 2C), 128.0 (d, 1C), 128.0 (d, 6C), 127.8 (d, 1C), 96.3 (d, 1C), 84.3 (d, 1C), 83.1 (d, 1C), 75.3 (d, 1C), 74.8 (t, 1C), 72.7 (t, 1C), 72.0 (t, 1C), 70.7 (t, 1C), 70.5 (t, 1C), 70.3 (d, 1C)

HRMS-ESI (m/z): $[M+Na]^+$

Calcd for $C_{28}H_{30}NaO_6$, 485.1940; found 485.1941.

EXAMPLE 4

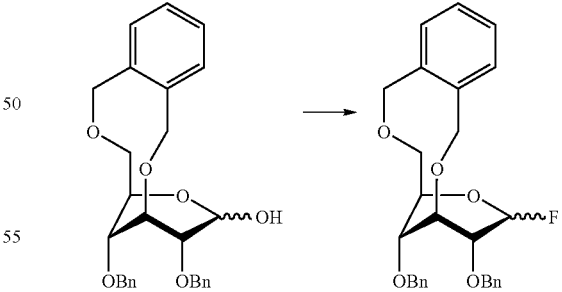

[Chem. 17]

Production of 2,4-di-O-benzyl-3,6-O-(o-xylylene)-D-glucopyranosyl fluoride (Dimethylamino)sulfur trifluoride (524 mg, 3.25 mmol) was added to a tetrahydrofuran (13 ml) solution of the 2,4-di-O-benzyl-3,6-O-(o-xylylene)-D-glucopyranose obtained in Example 3 under stirring. After the mixture was stirred for 30 minutes at room temperature, methanol (5 ml) was added, and the mixture was further stirred for 10 minutes at room temperature, followed by evaporation. The resulting residue was purified by silica gel column chromatography (20 g of SiO$_2$, n-hexane/ethyl acetate=15/1→8/1→4/1) to afford an anomeric mixture of the object compound (458 mg, total yield for 3 steps=76%, α/β=15/85) as a pale orange syrup, a part of which changed to a solid. The product was suspended in methanol/n-hexane with sonication to afford a white powder (359 mg, yield=59%, anomeric ratio=8/92). This powdery anomeric mixture was used for O-glucosidation without being purified.

In order to find individual physico-chemical properties of the a isomer and the β isomer, a part of these isomers was subjected to flash column chromatography (n-hexane/ethyl acetate=20/1→3/1) to separate the β-isomer (2,4-di-O-benzyl-3,6-O-(o-xylylene)-β-D-glucopyranosyl fluoride) and the α-isomer (2,4-di-O-benzyl-3,6-O-(o-xylylene)-α-D-glucopyranosyl fluoride) from each other.

The following are the physico-chemical properties of the β-isomer.

mp: 112° C. to 114° C.

$[\alpha]_D^{25}$=+84.5° (c=0.980, CHCl$_3$)

IR (ZnSe): 3065, 3030, 2907, 2872, 1113, 1074, 750, 698 cm$^{-1}$ $^1$H-NMR (400 MHz, CDCl$_3$): δ ppm 7.40-7.28 (m, 10H), 7.23-7.21 (m, 2H), 5.59 (dd, J=232, 5.5 Hz, 1H, H-1), 5.44 (d, J=10.1 Hz, 1H), 5.50 (d, J=10.1 Hz, 1H), 5.44 (d, J=10.1 Hz, 1H), 4.78 (d, J=11.7 Hz, 1H), 4.68 (d, J=11.7 Hz, 1H), 4.64 (d, J=11.7 Hz, 1H), 4.49 (d, J=11.7 Hz, 1H), 4.38 (d, J=10.1 Hz, 1H), 4.38 (d, J=10.1 Hz, 1H), 4.35 (brs, 1H, H-4), 4.24 (brd, J=3.0 Hz, 1H, H-5), 3.96 (br dd, J=3.0, 2.7 Hz, 1H, H-3), 3.91 (dd, J=13.8, 1.6 Hz, 1H, H-6a), 3.83 (ddd, J=13.8, 3.7, 1.2 Hz, 1H, H-6b), 3.78 (br dd, J=21.5, 5.5 Hz, H-2)

$^{13}$C-NMR (100 MHz, CDCl$_3$): δ ppm 138.1 (s, 1C), 137.8 (s, 1C), 137.1 (s, 1C), 136.4 (s, 1C), 129.8 (d, 1C), 128.8 (d, 1C), 128.7 (d, 2C), 128.6 (d, 2C), 128.1 (d, 1C), 128.1 (d, 1C), 128.0 (d, 7C), 127.9 (d, 1C), 110.2 (d.J=213 Hz, 1C), 83.4 (d, J=2.9 Hz, 1C), 82.0 (d, J=25.7 Hz, 1C), 75.5 (d, J=8.6 Hz, 1C), 74.9 (t, 1C), 72.8 (t, 1C), 72.1 (t, 1C), 70.9 (t, 1C), 70.4 (t, 1C), 70.0 (d, 1C)

HRMS-ESI (m/z): [M+Na]$^+$

Calcd for C$_{28}$H$_{29}$FO$_5$, 487.1897; found 487.1902.

The following are the physico-chemical properties of the α-isomer.

$[\alpha]_D^{25}$=+52.6° (c1.00, CHCl$_3$)

IR (ZnSe) 2919, 1455, 1393, 1113, 750, 698 cm$^{-1}$ $^1$H-NMR (400 MHz, CDCl$_3$) δ ppm: 3.58 (dd, J=13.3 Hz, J=3.2 Hz, 1H), 3.77 (d, J=13.3 Hz, 1H), 3.86 (br dd, J=5.2 Hz, J=21.7 Hz, 1H), 3.95 (br s, 1H), 4.26 (d, J=10.3 Hz, 1H), overlapping with 4.27-4.29 (m, 1H), 4.33 (d, J=10.5 Hz, 1H), overlapping with 4.30-4.32 (br s, 1H), 4.54 (d, J=12.4 Hz, 1H), 4.68 (d, J=12.4 Hz, 2H), 4.77 (d, J=12.4 Hz, 1H), 4.96 (d, J=10.5 Hz, 1H), 5.25 (d, J=10.3 Hz, 1H), 5.81 (dd, J=54.1 Hz, J=5.5 Hz, 1H), 7.06-7.12 (m, 1H), 7.15-7.36 (m, 11H), 7.38-7.43 (m, 2H)

$^{13}$C-NMR (100 MHz, CDCl$_2$) δ ppm: 69.0, 69.6, 70.3, 71.9, 72.3, 73.5, 73.9, 75.2 (d, J=23.0 Hz), 77.2 (d, J=3.8 Hz), 103.4 (d, J=234.8 Hz), 127.8, 127.8, 127.8, 127.9, 128.0, 128.0, 128.4, 128.4, 129.1, 129.7, 136.5, 136.7, 137.9, 137.9

HRMS-ESI (m/z): [M+Na]$^+$

Calcd for C$_{28}$H$_{29}$FO$_5$, 487.1897; found 487.1888.

EXAMPLE 5

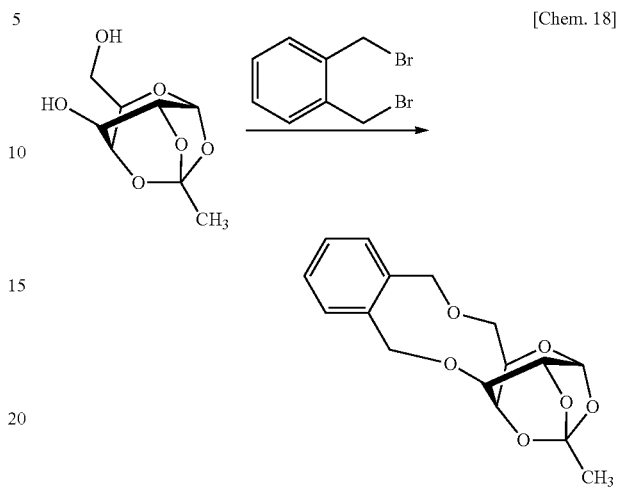

[Chem. 18]

Production of 1,2,4-O-ethylidyne-3,6-O-(o-xylylene)-α-D-glucopyranose

60% NaH in mineral oil (1.18 g, 0.710 g as NaH, 29.4 mmol) was added to toluene (180 ml), and the mixture was stirred. α-o-dibromoxylene (2.59 g, 9.80 mmol) was added to the mixture at room temperature. A dimethylformamide solution (60 ml) of 1,2,4-O-ethylidyne-α-D-glucopyranose (1.00 g, 4.90 mmol) was dropped into this mixture for an hour at 80° C. to 85° C. After that, the liquid was stirred for an hour at the same temperature, and the resulting mixture was cooled to 0° C. The reaction was quenched by adding an aqueous saturated ammonium chloride solution (20 ml), and then water (300 ml) was added. The mixture was extracted with ethyl acetate (150 ml×3), and the extract was dried over magnesium sulfate, and concentrated under reduced pressure. The crude product was purified by flash column chromatography (silica gel 100 g, ethyl acetate/n-hexane=5/95) to afford 1,2,4-O-ethylidyne-3,6-O-(o-xylylene)-α-D-glucopyranose (1.02 g, yield=68%) as a white amorphous solid.

The following are the physico-chemical properties of the object compound.

mp: 131° C. to 133° C.

$[\alpha]_D^{24}$=+126.9° (c=1.09, CHCl$_3$)

IR (ZnSe): 3009, 2953, 2899, 2859, 1134, 1082, 1048, 752 cm$^{-1}$ $^1$H-NMR (400 MHz, C$_6$D$_6$): δ ppm 7.03-6.96 (m, 2H), 6.93-6.86 (m, 2H), 5.56 (d, J=4.9 Hz, 1H), 5.52 (d, J=10.1 Hz, 1H), 4.91 (d, J=9.4 Hz, 1H), 4.61 (br d, J=3.1 Hz, 1H), 4.47 (dd, J=4.3, 2.1 Hz, 1H), 4.18 (d, J=10.1 Hz, 1H), 4.11 (dd, J=4.9, 2.1 Hz, 1H), 3.88 (d, J=9.4 Hz, 1H), 3.85 (dd, J=4.3, 1.8 Hz, 1H), 3.61 (dd, J=14.2 Hz, J=1.4 Hz, 1H), 3.53 (dd, J=14.2 Hz, J=3.1 Hz, 1H)

$^{13}$C-NMR (100 MHz, C$_6$D$_6$): δ ppm 138.0 (s, 1C), 136.7 (s, 1C), 128.7 (d, 1C), 128.7 (d, 1C), 127.8 (d, 1C), 127.4 (d, 1C), 119.9 (s, 1C), 98.1 (d, 1C), 79.7 (d, 1C), 74.8 (t, 1C), 74.1 (d, 1C), 72.3 (d, 1C), 71.9 (t, 1C), 70.5 (d, 1C), 69.3 (t, 1C), 20.9 (q, 1C)

HRMS-ESI (m/z): [M+Na]$^+$

Calcd for C$_{16}$H$_{18}$NaO$_6$, 329.1001; found 329.1010.

EXAMPLE 6

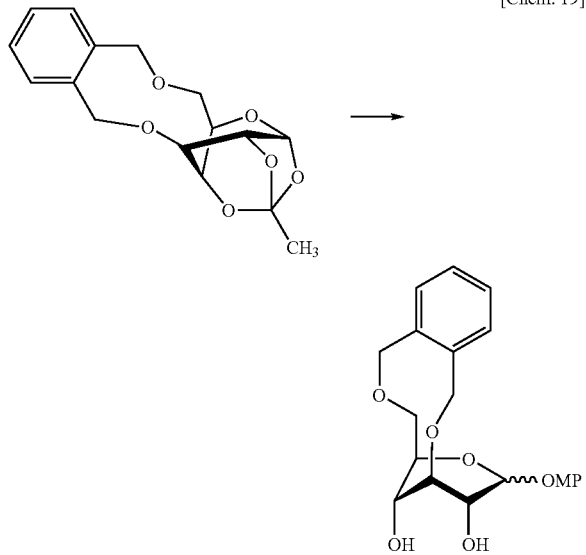

Production of 4-methoxyphenyl 3,6-O-(o-xylylene)-D-glucopyranoside

A mixture of 1,2,4-O-ethylidyne-3,6-O-(o-xylylene)-α-D-glucopyranose (400 mg, 1.30 mmol) and 4-methoxyphenol (1.48 g, 11.9 mmol) was heated at 100° C. to 110° C. for 3.5 hours. The resulting substance was dissolved in methanol (15 ml), and then powdered 4 Å molecular sieve (2.00 g) was added thereto. After stirring at 60° C. for 6 hours, the obtained mixture was filtrated through Celite, followed by concentration under reduced pressure.

The crude product was purified by flash column chromatography (silica gel 100 g, ethyl acetate/n-hexane=5/95) to afford 4-methoxyphenyl 3,6-O-(o-xylylene)-α-D-glucopyranoside (99.2 g, yield=20%) as a yellow amorphous solid, and 4-methoxyphenyl 3,6-O-(o-xylylene)-β-D-glucopyranoside (303 mg, yield=60%) as a yellow amorphous solid.

The following are the physico-chemical properties of the object compound.

physico-chemical properties of α-isomer;
mp: 61° C. to 64° C.
$[\alpha]_D^{24}$=−40.3° (c=0.62, CHCl$_3$)
IR (ZnSe): 3422, 2932, 2878, 1509, 1217, 1115, 1032, 758 cm$^{-1}$
$^1$H-NMR (400 MHz, CDCl$_3$): δ ppm 7.33-7.20 (m, 4H), 6.98-6.94 (m, 2H), 6.82-6.78 (m, 2H), 5.52 (d, J=2.3 Hz, 1H), 5.02 (d, J=9.9 Hz, 1H), 4.89 (d, J=12.6 Hz, 1H), 4.74 (d, J=12.6 Hz, 1H), 4.54 (d, J=9.9 Hz, 1H), 4.39 (br dd, J=7.3, 6.2 Hz, 1H), 4.33 (br d, J=8.9 Hz, 1H), 4.15-4.07 (m, 4H), 3.91 (dd, J=10.3 Hz, J=6.2 Hz, 1H), 3.75 (s, 3H), 3.07 (d, J=1.4 Hz, 1H)
$^{13}$C-NMR (100 MHz, CDCl$_3$): δ ppm 156.5 (s, 1C), 150.6 (s, 1C), 137.2 (s, 1C), 136.1 (s, 1C), 131.3 (d, 1C), 130.1 (d, 1C), 129.1 (d, 1C), 128.5 (d, 1C), 118.0 (d, 2C), 114.8 (d, 2C), 93.9 (d, 1C), 79.5 (d, 1C), 75.2 (d, 1C), 74.2 (t, 1C), 70.4 (t, 1C), 70.1 (t, 1C), 68.7 (t, 1C), 63.4 (d, 1C), 55.8 (q, 1C)
HRMS-ESI (m/z): [M+Na]$^+$
Calcd for C$_{21}$H$_{24}$NaO$_7$, 411.1420; found 411.1432.

Physico-chemical properties of β-isomer;
mp: 88° C. to 90° C.
$[\alpha]_D^{24}$=−61.1° (c=1.04, CHCl$_3$)
IR (ZnSe): 3407, 2907, 2874, 1509, 1217, 1111, 1090, 1051, 1036, 752 cm$^{-1}$
$^1$H-NMR (400 MHz, CDCl$_3$): δ ppm 7.24-7.12 (m, 4H), 6.98-6.94 (m, 2H), 6.84-6.80 (m, 2H), 5.44 (d, J=10.3 Hz, 1H), 5.16 (d, J=5.3 Hz, 1H), 5.15 (d, J=10.3 Hz, 1H), 4.69 (m, 1H), 4.54 (d, J=10.3 Hz, 1H), 4.42 (d, J=10.3 Hz, 1H), 4.13 (br dd, J=3.9, 2.5 Hz, 1H), 4.07 (br dd, J=8.5, 5.3 Hz, 1H), 3.99 (dd, J=13.3 Hz, J=3.9 Hz, 1H), 3.94 (dd, J=13.3 Hz, J=2.5 Hz, 1H), 3.86 (br d, J=3.4 Hz, 1H), 3.77 (s, 3H), 2.84 (d, J=8.5 Hz, 1H), 2.45 (d, J=5.3 Hz, 1H)
$^{13}$C-NMR (100 MHz, CDCl$_3$): δ ppm 155.0 (s, 1C), 151.2 (s, 1C), 137.0 (s, 1C), 136.2 (s, 1C), 129.6 (d, 1C), 128.9 (d, 1C), 128.0 (d, 1C), 127.8 (d, 1C), 117.8 (d, 2C), 114.5 (d, 2C), 102.3 (d, 1C), 83.1 (d, 1C), 78.5 (d, 1C), 74.9 (t, 1C), 74.5 (d, 1C), 71.2 (t, 1C), 70.3 (t, 1C), 64.6 (d, 1C), 55.7 (q, 1C)
HRMS-ESI (m/z): [M+Na]$^+$
Calcd for C$_{21}$H$_{24}$NaO$_7$, 411.1420; found 411.1433.

EXAMPLE 7

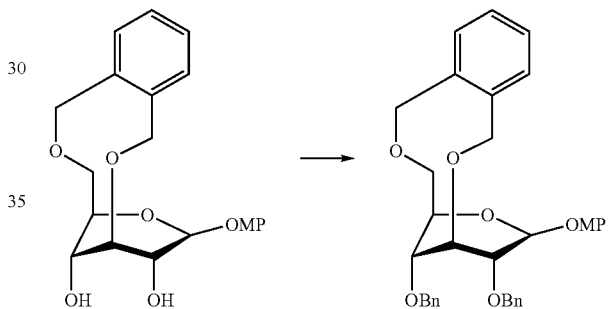

Production of 4-methoxyphenyl 2,4-di-O-benzyl-3,6-O-(o-xylylene)-β-D-glucopyranoside A mixture of 4-methoxyphenyl 3,6-O-(o-xylylene)-β-D-glucopyranoside (172 mg, 0.44 mmol), 60% NaH in mineral oil (106 mg, 63.6 mg as NaH, 2.64 mmol) and dimethylformamide (8.0 ml) was stirred, and benzyl bromide (301 mg, 1.76 mmol) was added thereto at room temperature. The mixture was stirred for 5 hours at 80° C. to 85° C. Then, the reaction was quenched by adding an aqueous saturated ammonium chloride solution (2.0 ml), and water (40 ml) was added. The mixture was extracted with ethyl acetate (50 ml×3). The ethyl acetate layer was successively washed with water (50 ml×1) and saturated saline (50 ml×1), followed by drying over magnesium sulfate and filtration. The filtrate was concentrated and the residue was purified by flash column chromatography (silica gel 10 g, ethyl acetate/n-hexane=5/95→20/80) to afford 4-methoxyphenyl 2,4-di-O-benzyl-3,6-O-(o-xylylene)-β-D-glucopyranoside (194 mg, yield=77%) as a yellow syrup.

The following are the physico-chemical properties of the object compound.
mp: 68° C. to 70° C.
$[\alpha]_D^{24}$=+11.0° (c=1.29, CHCl$_3$)
IR (ZnSe): 3063, 3029, 2903, 2872, 1455, 1215, 1113, 1044, 750 cm$^{-1}$ $^1$H-NMR (400 MHz, CDCl$_3$): δ ppm 7.40-7.26 (m, 10H), 7.21-7.10 (m, 4H), 6.96-6.92 (m, 2H), 6.83-6.79 (m, 2H), 5.57 (d, J=9.9 Hz, 1H), 5.27 (d, J=6.6 Hz, 1H), 5.13 (d, J=10.1 Hz, 1H), 4.81 (d, J=12.1 Hz, 1H), 4.74 (d, J=12.1 Hz, 1H), 4.70 (d, J=11.7 Hz, 1H), 4.53 (d, J=11.7 Hz, 1H), 4.45 (br s, 1H), 4.35 (d, J=10.1 Hz, 1H), 4.30 (d, J=9.9 Hz, 1H), 4.22 (br s, 1H), 4.01 (br d, J=2.8 Hz, 1H), 3.90 (br d, J=6.6 Hz, 1H), 3.83 (br d, J=13.5 Hz, 1H), 3.79 (br d, J=13.5 Hz, 1H), 3.77 (s, 3H)

$^{13}$C-NMR (100 MHz, CDCl$_3$): δ ppm 155.1 (s, 1C), 151.4 (s, 1C), 138.6 (s, 1C), 138.0 (s, 1C), 137.1 (s, 1C), 136.5 (s, 1C), 129.6 (d, 1C), 128.6 (d, 1C), 128.6 (d, 2C), 128.4 (d, 2C), 128.0 (d, 1C), 127.9 (d, 2C), 127.9 (d, 2C), 127.8 (d, 2C), 127.7 (d, 1C), 118.0 (d, 2C), 114.6 (d, 2C), 101.2 (d, 1C), 83.1 (d, 1C), 82.3 (d, 1C), 75.4 (d, 1C), 75.0 (t, 1C), 72.9 (t, 1C), 72.0 (t, 1C), 70.6 (t, 1C), 70.5 (t, 1C), 70.3 (d, 1C), 55.8 (q, 1C)

HRMS-ESI (m/z): [M+Na]$^+$

Calcd for C$_{35}$H$_{36}$NaO$_7$, 591.2359; found 591.2345.

EXAMPLE 8

[Chem. 21]

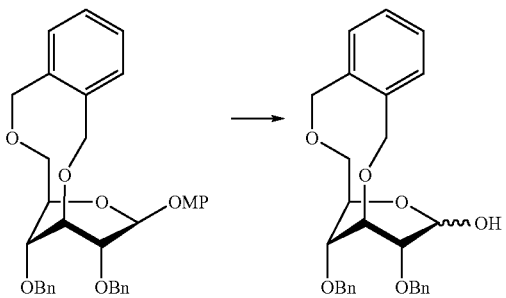

Production of 2,4-di-O-benzyl-3,6-O-(o-xylylene)-D-glucopyranose

Cerium(IV)sulfate (565 mg, 1.70 mmol) was added to a mixture of 4-methoxyphenyl 2,4-di-O-benzyl-3,6-O-(o-xylylene)-β-D-glucopyranoside (194 mg, 0.340 mmol), acetonitrile (5.0 ml) and water (2.5 ml) under stirring at room temperature. After stirring the resulting mixture for 19 hours at the same temperature, a 10% sodium thiosulfate aqueous solution (15 ml) was added to quench the reaction. The reaction mixture was extracted with ethyl acetate (20 ml×3). The organic layer was successively washed with water (20 ml×1) and saturated saline (20 ml×1), followed by drying over magnesium sulfate and filtration. The filtrate was concentrated, and the residue was purified by flash column chromatography (silica gel 10 g, ethyl acetate/n-hexane=5/95→40/60) to afford 2,4-di-O-benzyl-3,6-O-(o-xylylene)-D-glucopyranose (129 mg, yield=82%) as a white solid. The $^1$H-NMR spectrum of the obtained compound coincided with that of the 2,4-di-O-benzyl-3,6-O-(o-xylylene)-D-glucopyranose obtained in Example 3.

EXAMPLE 9

[Chem. 22]

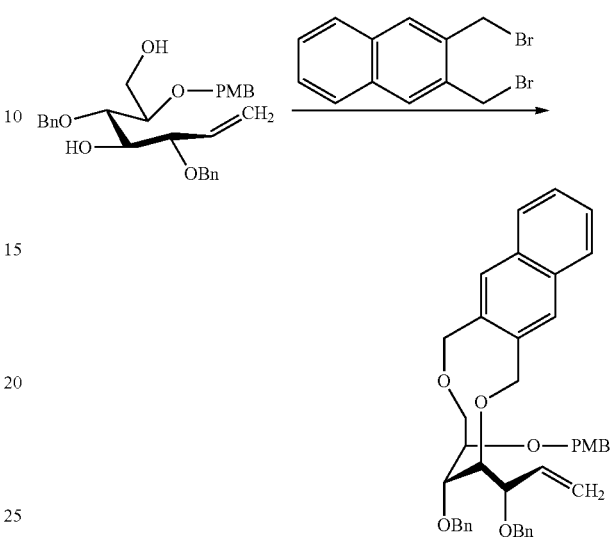

Production of 1,2-dideoxy-3,5-di-O-benzyl-4,7-O-{2,3-naphthalene(bismethylene)}-6-O-(4-methoxybenzyl)-D-gluco-hept-1-enitol A mixture of 60% NaH in mineral oil (260 mg, 156 mg as NaH, 6.50 mmol), 2,3-bis bromomethyl naphthalene (680 mg, 2.17 mmol) and toluene (81 ml) was stirred. A dimethylformamide (27 ml) solution of 1,2-dideoxy-6-O-(4-methoxybenzyl)-3,5-di-O-benzyl-D-gluco-hept-1-enitol (518 mg, 1.08 mmol) was dropped into the stirred mixture for 1.5 hours. The mixture was further stirred for 30 minutes at the same temperature. Then, an aqueous saturated ammonium chloride solution (25 ml) was added thereto to quench the reaction. The mixture was extracted with ethyl acetate (100 ml×2). The organic layer was successively washed with water (100 ml×2) and saturated saline (100 ml×1), and then dried over magnesium sulfate. The extract was concentrated and purified by chromatography (silica gel 30 g, ethyl acetate/n-hexane=1/15→1/8) to afford 1,2-dideoxy-3,5-di-O-benzyl-4,7-O-{2,3-naphthalene(bismethylene)}-6-O-(p-methoxybenzyl)-D-gluco-hept-1-enitol (423 mg, 0.671 mmol) as a yellow solid.

The following are the physico-chemical properties of the object compound.

mp: 87° C. to 89° C.

[α]$_D^{23}$=−69.7° (c=1.16, CHCl$_3$)

IR (ZnSe): 3061, 3031, 3007, 2932, 1514, 1248, 1090, 756, 698 cm$^{-1}$ $^1$H-NMR (400 MHz, CDCl$_3$): δ ppm 7.89 (s, 1H), 7.85-7.79 (m, 2H), 7.61 (s, 1H), 7.51-7.25 (m, 12H), 7.03 (br ddd, J=9.6, 4.6, 2.8 Hz, 2H), 6.70 (br ddd, J=9.6, 4.8, 2.8 Hz, 2H), 5.49 (ddd, J=18.1, 10.3, 7.8 Hz, 1H), 5.23 (d, J=11.7 Hz, 1H), 5.17 (br dd, J=10.3, 1.8 Hz, 1H), 5.14 (br dd, J=18.1, 1.4 Hz, 1H), 4.95 (d, J=11.7 Hz, 1H), 4.95 (d, J=12.1 Hz, 1H), 4.83 (d, J=12.1 Hz, 1H), 4.73 (d, J=11.7 Hz, 1H), 4.62 (d, J=11.7 Hz, 1H), 4.56 (dd, J=12.6, 3.9 Hz, 1H), 4.56 (d, J=11.9 Hz, 1H), 4.49 (d, J=11.7 Hz, 1H), 4.36 (d, J=11.7 Hz, 1H), 4.22 (dd, J=8.5, 7.8 Hz, 1H), 4.17 (d, J=11.9 Hz, 1H), 3.95 (dd, J=12.6, 3.7 Hz, 1H), 3.74 (s, 3H), 3.57 (br d, J=1.6 Hz, 1H), 3.42 (dd, J=8.5, 1.6 Hz, 1H), 3.30 (br dd, J=3.9, 3.7 Hz, 1H)

$^{13}$C-NMR (100 MHz, CDCl$_3$): δ ppm 159.1 (s, 1C), 139.1 (s, 1C), 138.8 (s, 1C), 137.2 (s, 1C), 135.2 (d, 1C), 134.5 (s, 1C), 133.7 (s, 1C), 132.9 (s, 1C), 130.8 (d, 1C), 130.7 (s, 1C), 130.5 (d, 1C), 129.2 (d, 2C), 128.6 (d, 2C), 128.3 (d, 2C), 128.3 (d, 2C), 128.0 (d, 2C), 127.8 (d, 2C), 127.7 (d, 1C), 127.6 (d, 1C), 126.6 (d, 1C), 126.5 (d, 1C), 119.6 (t, 1C), 113.8 (d, 2C), 83.9 (d, 1C), 83.1 (d, 1C), 81.7 (d, 1C), 79.2 (d, 1C), 73.9 (t, 1C), 73.3 (t, 2C), 72.5 (t, 1C), 71.4 (t, 1C), 71.3 (t, 1C), 55.4 (q, 1C)

HRMS-ESI (m/z): [M+Na]$^+$

Calcd for C$_{41}$H$_{42}$NaO$_6$, 653.2879; found 653.2878.

EXAMPLE 10

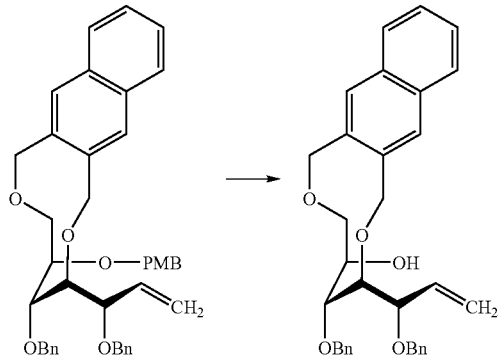

[Chem. 23]

Production of 1,2-dideoxy-3,5-di-O-benzyl-4,7-O-{2,3-naphthalene(bismethylene)}-D-gluco-hept-1-enitol ZrCl$_4$ (180 mg, 0.775 mmol) was added to an acetonitrile (8 ml) solution of 1,2-dideoxy-3,5-di-O-benzyl-4,7-O-{2,3-naphthalene (bismethylene)}-6-O-(p-methoxybenzyl)-D-gluco-hept-1-enitol (488 mg, 0.775 mmol) under stirring at room temperature. The obtained mixture was stirred for 40 minutes at the same temperature. An aqueous saturated sodium bicarbonate solution was added thereto to quench the reaction. The mixture was extracted with ethyl acetate (25 ml×2). The organic layer was successively washed with an aqueous saturated sodium bicarbonate solution (25 ml×1) and saturated saline (25 ml×1). The extract was concentrated, and purified by silica gel column chromatography (silica gel 30 g, ethyl acetate/n-hexane=1/6→1/2) to afford 1,2-dideoxy-3,5-di-O-benzyl-4,7-O-{2,3-naphthalene(bismethylene)}-D-gluco-hept-1-enitol (332 mg, 0.650 mmol) as an amorphous solid.

The following are the physico-chemical properties of the object compound.

mp: 140° C. to 143° C.

$[α]_D^{24}$=−3.0° (c=1.08, CHCl$_3$)

IR (ZnSe): 3395, 3061, 3031, 2932, 2888, 1455, 1088, 754, 698 cm$^{-1}$ $^1$H-NMR (400 MHz, CDCl$_3$): δ ppm 7.78 (dd, J=6.2, 3.4 Hz, 2H), 7.69 (s, 2H), 7.47 (dd, J=6.2, 3.2 Hz, 2H), 7.40-7.22 (m, 10H), 5.78 (ddd, J=17.4, 10.3, 7.8 Hz, 1H), 5.35 (br d, J=10.3 Hz, 1H), 5.31 (br d, J=17.4 Hz, 1H), 5.13 (d, J=10.5 Hz, 1H), 5.11 (d, J=13.1 Hz, 1H), 4.89 (d, J=10.5 Hz, 1H), 4.67 (d, J=13.1 Hz, 1H), 4.67 (d, J=11.7 Hz, 1H), 4.56 (d, J=11.9 Hz, 1H), 4.51 (d, J=11.7 Hz, 1H), 4.49 (d, J=11.9 Hz, 1H), 4.27 (dd, J=7.8, 7.8 Hz, 1H), 4.04 (dd, J=10.5, 6.6 Hz, 1H), 3.95 (dd, J=7.8, 2.3 Hz, 1H), 3.81 (ddd, J=8.7, 6.6, 3.0 Hz, 1H), 3.69 (dd, J=10.5, 3.0 Hz, 1H), 3.68 (br d, J=2.3 Hz, 1H), 2.81 (d, J=8.7 Hz, 1H)

$^{13}$C-NMR (100 MHz, CDCl$_3$): δ ppm 138.7 (s, 1C), 138.5 (s, 1C), 136.0 (s, 1C), 135.5 (d, 1C), 134.8 (s, 1C), 133.4 (s, 1C), 133.2 (s, 1C), 131.1 (d, 1C), 128.9 (d, 1C), 128.6 (d, 2C), 128.5 (d, 2C), 128.0 (d, 2C), 128.0 (d, 2C), 127.9 (d, 1C), 127.8 (d, 1C), 127.7 (d, 2C), 126.6 (d, 1C), 126.4 (d, 1C), 120.0 (t, 1C), 83.8 (d, 1C), 83.0 (d, 1C), 78.6 (d, 1C), 75.4 (t, 1C), 73.9 (t, 1C), 73.1 (t, 1C), 72.8 (d, 1C), 72.7 (t, 1C), 71.0 (t, 1C)

HRMS-ESI (m/z): [M+Na]$^+$

Calcd for C$_{33}$H$_{34}$NaO$_5$, 533.2304; found 533.2299.

EXAMPLE 11

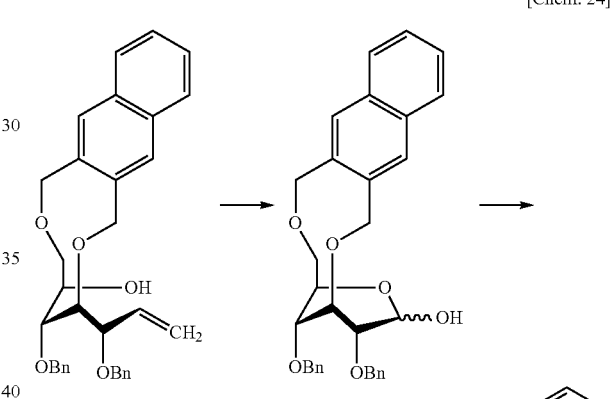

[Chem. 24]

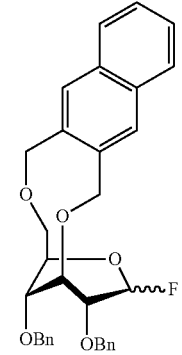

Production of 2,4-di-O-benzyl-3,6-O-{2,3-naphthalene(bismethylene)}-D-glucopyranosyl fluoride An aqueous solution of osmium tetraoxide (25 mg/ml solution in distilled water, 0.39 ml, 38.1 mmol) was added to a mixture of 1,2-dideoxy-3,5-di-O-benzyl-4,7-O-{2,3-naphthalene(bismethylene)}-D-gluco-hept-1-enitol (97.3 mg, 191 mmol), 4-methylmorpholine-N-oxide (89.3 mg, 762 mmol) and acetone (2 ml). After stirring the mixture for 5 hours at room temperature, sodium periodate (102 mg, 476 mmol) and distilled water (0.40 ml) were added, followed by further stirring for 40 minutes at room temperature. The resulting mixture was filtered through Celite, and concentrated. The residue was diluted with ethyl acetate (50 ml), successively washed with a 10% sodium thiosulfate aqueous solution (30 ml×1), water (30 ml×1) and a saline solution (30 ml×1), dried over magnesium sulfate and filtered. The filtrate was concentrated to afford 2,4-di-O-benzyl-3,6-O-{2,3-naphthalene(bismethylene)}-D-glucopyranose as a white solid. The solid was used for the next reaction without being purified.

(Dimethylamino)sulfur trifluoride (92.1 mg, 572 mmol) was added to a tetrahydrofuran (2 ml) solution of 2,4-di-β-benzyl-3,6-O-{2,3-naphthalene(bismethylene)}-D-glucopyranose under stirring. After the mixture was stirred for 6 hours at room temperature, methanol (1 ml) was added, and the mixture was further stirred for an hour at room temperature, followed by concentration. The resulting residue was diluted with ethyl acetate (30 ml), successively washed with water (30 ml), an aqueous saturated sodium bicarbonate solution (25 ml) and saturated saline (25 ml), and dried over magnesium sulfate and filtered. The filtrate was concentrated and the resulting residue was purified by silica gel column chromatography (silica gel, 10 g, ethyl acetate/n-hexane=1/20→1/12) to afford 2,4-di-O-benzyl-3,6-O-{2,3-naphthalene(bismethylene)}-D-glucopyranosyl fluoride (68.3 mg, total yield for 3 steps=70%, α/β=16/84) as a white crystal.

The following are the physico-chemical properties of the object compound.

physico-chemical properties of α-isomer;
mp: 166° C. to 168° C.
$[\alpha]_D^{24}$=+91.9° (c=0.78, CHCl$_3$)
IR (ZnSe): 2915, 2872, 1455, 1113, 743, 698 cm$^{-1}$
$^1$H-NMR (400 MHz, CDCl$_3$): δ ppm 7.77-7.73 (m, 2H), 7.64 (s, 1H), 7.58 (s, 1H), 7.47-7.41 (m, 4H), 7.36-7.24 (m, 8H), 5.82 (dd, J=53.8, 5.5 Hz, 1H, H-1), 5.39 (d, J=10.1 Hz, 1H), 5.13 (d, J=10.3 Hz, 1H), 4.78 (d, J=12.1 Hz, 1H), 4.70 (d, J=12.4 Hz, 1H), 4.69 (d, J=12.1 Hz, 1H), 4.51 (d, J=12.4 Hz, 1H), 4.47 (d, J=10.3 Hz, 1H), 4.43 (d, J=10.1 Hz, 1H), 4.38 (br s, 1H, H-4), 4.35 (br d, J=1.6 Hz, 1H, H-5), 3.98 (br s, 1H, H-3), 3.85 (br dd, J=27.3, 5.5 Hz, 1H, H-2), 3.82 (br d, J=13.5 Hz, 1H, H-6a), 3.65 (dd, J=13.5, 3.4 Hz, 1H, H-6b)
$^{13}$C-NMR (100 MHz, CDCl$_3$): δ ppm 138.1 (s, 1C), 138.1 (s, 1C), 134.6 (s, 1C), 134.5 (s, 1C), 133.0 (s, 1C), 128.9 (s, 1C), 128.6 (d, 4C), 128.4 (d, 1C), 128.2 (d, 2C), 128.1 (d, 3C), 128.0 (d, 1C), 127.8 (d, 1C), 127.6 (d, 1C), 126.5 (d, 1C), 126.5 (d, 1C), 103.6 (d, J=235 Hz, 1C), 77.5 (d, J=3.8 Hz, 1C), 75.7 (d, J=23.0 Hz, 1C), 74.4 (d, 1C), 73.5 (d, 1C), 72.5 (t, 1C), 72.2 (t, 1C), 70.7 (t, 1C), 69.7 (t, 1C), 69.5 (t, 1C)
HRMS-ESI (m/z): [M+Na]$^+$
Calcd for C$_{32}$H$_{31}$FNaO$_5$, 537.2053; found 537.2066.

physico-chemical properties of β-isomer;
mp: 195° C. to 197° C.
[α]D25=+76.3° (c=0.88, CHCl3)
IR (KBr): 2909, 2878, 2855, 1111, 1069 cm−1
1H-NMR (400 MHz, CDCl$_3$): δ ppm 7.77 (dd, J=6.2, 3.4 Hz, 2H), 7.62 (s, 2H), 7.46 (dd, J=6.2, 3.4 Hz, 2H), 7.41-7.26 (m, 10H), 5.60 (dd, J=53.0, 5.7 Hz, 1H, H-1), 5.56 (d, J=10.8 Hz, 1H), 5.18 (d, J=9.9 Hz, 1H), 4.79 (d, J=11.7 Hz, 1H), 4.69 (d, J=11.7 Hz, 1H), 4.65 (d, J=11.7 Hz, 1H), 4.54 (d, J=10.8 Hz, 1H), 4.53 (d, J=9.9 Hz, 1H), 4.50 (d, J=11.7 Hz, 1H), 4.40 (br s, 1H, H-3), 4.26 (br d, J=3.2 Hz, 1H, H-5), 4.02 (dd, J=3.0, 2.8 Hz, 1H, H-4), 3.96 (dd, J=13.7, 1.4 Hz, 1H, H-6a), 3.88 (ddd, J=13.7, 3.7, 1.1 Hz, 1H, H-6b), 3.80 (dd, J=22.0, 5.7 Hz, 1H, H-2)
13C-NMR (100 MHz, CDCl3): δ ppm 138.1 (s, 1C), 137.8 (s, 1C), 134.9 (s, 1C), 134.2 (s, 1C), 133.0 (s, 1C), 132.9 (s, 1C), 128.8 (d, 1C), 128.7 (d, 2C), 128.6 (d, 2C), 128.1 (d, 1C), 128.0 (d, 2C), 128.0 (d, 3C), 127.9 (d, 1C), 127.8 (d, 1C), 127.6 (d, 1C), 126.5 (d, 1C), 126.4 (d, 1C), 110.3 (d, J=213 Hz, 1C), 83.5 (d, J=2.9 Hz, 1C), 82.1 (d, J=25.9 Hz, 1C), 75.6 (d, J=7.8 Hz, 1C), 75.1 (t, 1C), 72.8 (t, 1C), 72.2 (t, 1C), 71.0 (t, 1C), 70.5 (t, 1C), 70.1 (d, 1C)
HRMS-ESI (m/z): [M+Na]+
Calcd for C$_{32}$H$_{31}$FNaO$_5$, 537.2053; found 537.2075.

EXAMPLE 12

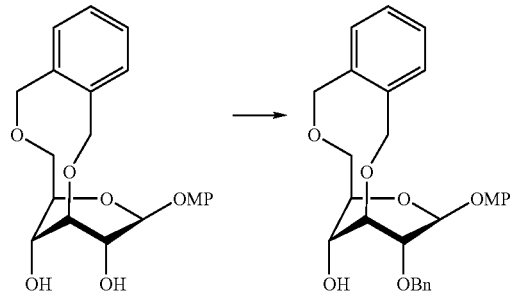

[Chem. 25]

Production of 4-methoxyphenyl 2-O-benzyl-3,6-O-(o-xylylene)-β-D-glucopyranoside

A mixture of 4-methoxyphenyl 3,6-O-(o-xylylene)-D-glucopyranoside (109 mg, 0.280 mmol), 60% NaH in mineral oil (44.8 mg, 26.9 mg as NaH, 1.12 mmol) and tetrahydrofuran (5.0 ml) was stirred. After the hydrogen discharge stopped, CuCl$_2$ (41.7 mg, 0.31 mmol) was added. After 15 minutes, a green-colored copper chelating solution was obtained. Then, benzyl bromide (95.8 mg, 0.560 mmol) and tetra-n-butylammonium iodide (21.2 mg, 56.0 mmol) were added to the solution. The obtained mixture was subjected to heating under reflux for 19 hours, and cooled. The reaction was quenched with a dilute ammonium hydroxide aqueous solution (5 ml), followed by evaporation to dryness. An ethyl acetate (20 ml) solution of the residue was washed with a dilute ammonium hydroxide aqueous solution until the aqueous layer became colorless, and then washed with water. The extract was dried over magnesium sulfate and filtered. The filtrate was concentrated, and the resulting residue was purified by flash column chromatography (silica gel 10 g, ethyl acetate/n-hexane=5/95→50/50) to afford 4-methoxyphenyl 2-O-benzyl-3,6-O-(o-xylylene)-β-D-glucopyranoside (45.0 mg, yield=36%) as a white solid.

The following are the physico-chemical properties of the object compound.

mp: 71° C. to 73° C.
$[\alpha]_D^{22}$=−11.5° (c=1.01, CHCl$_3$)
IR (ZnSe): 3450, 2907, 2870, 1507, 1215, 1111, 1049, 970, 828, 750 cm$^{-1}$
$^1$H-NMR (400 MHz, CDCl$_3$): δ ppm 7.37-7.29 (m, 5H), 7.22-7.11 (m, 4H), 6.97-6.92 (m, 2H), 6.86-6.82 (m, 2H), 5.52 (d, J=10.0 Hz, 1H), 5.24 (d, J=10.0 Hz, 1H), 5.23 (d, J=5.3 Hz, 1H), 4.75 (d, J=11.7 Hz, 1H), 4.72 (d, J=11.7 Hz, 1H), 4.71-4.67 (m, 1H), 4.45 (d, J=10.0 Hz, 1H), 4.37 (d, J=10.0 Hz, 1H), 4.18 (br s, 1H), 3.99-3.95 (m, 2H), 3.90 (dd, J=13.3 Hz, J=1.6 Hz, 1H), 3.90 (br d, J=3.2 Hz, 1H), 3.78 (s, 3H), 2.82 (d, J=7.6 Hz, 1H)
$^{13}$C-NMR (100 MHz, CDCl$_3$): δ ppm 154.9 (s, 1C), 150.9 (s, 1C), 137.2 (s, 1C), 136.9 (s, 1C), 136.1 (s, 1C), 129.2 (d, 1C), 128.6 (d, 1C), 128.3 (d, 2C), 127.9 (d, 3C), 127.7 (d, 1C), 127.5 (d, 1C), 117.6 (d, 2C), 114.4 (d, 2C), 101.0 (d, 1C), 83.8 (d, 1C), 81.2 (d, 1C), 76.8 (d, 1C), 74.6 (t, 1C), 72.7 (t, 1C), 70.6 (t, 1C), 69.9 (t, 1C), 63.5 (d, 1C), 55.5 (q, 1C)

HRMS-ESI (m/z): [M+Na]$^+$

Calcd for $C_{28}H_{30}NaO_7$, 501.1889; found 501.1890.

EXAMPLE 13

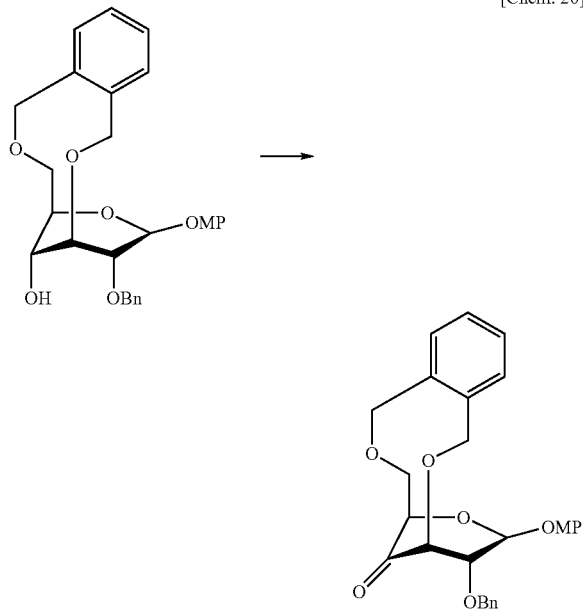

[Chem. 26]

Production of 4-methoxyphenyl 2-O-benzyl-3,6-O-(o-xylylene)-β-D-xylo-hexopyranoside-4-ulose Dess-Martin periodinane (188 mg, 0.443 mmol) was added to a dichloromethane (3.0 ml) solution of 4-methoxyphenyl 2-O-benzyl-3,6-O-(o-xylylene)-β-D-glucopyranoside (103 mg, 0.215 mmol) at 0° C. The mixture was stirred for 1.5 hours at the same temperature, and for another 1.5 hours at room temperature. An aqueous saturated sodium thiosulfate solution (3.0 ml) and an aqueous saturated sodium bicarbonate solution (3.0 ml) were added thereto to quench the reaction. The reaction mixture was extracted with methylene chloride (6.0 ml×3). The organic layer was successively washed with an aqueous sodium bicarbonate solution (10 ml×1), water (10 ml×1) and saturated saline (10 ml×1), followed by drying over magnesium sulfate and filtration. The filtrate was concentrated, and the residue was purified by flash column chromatography (silica gel 10 g, ethyl acetate/n-hexane=5/95→20/80) to afford 4-methoxyphenyl 2-O-benzyl-3,6-O-(o-xylylene)-β-D-xylo-hexopyranoside-4-ulose (102 mg, 100%) as a white amorphous solid.

The following are the physico-chemical properties of the object compound.

mp: 53° C. to 55° C.

$[\alpha]_D^{22}$=+10.8° (c=0.78, CHCl$_3$)

IR (ZnSe): 2905, 1736, 1507, 1466, 1456, 1246, 1217, 1183, 1102, 1040, 980, 828, 752, 698 cm$^{-1}$ $^1$H-NMR (400 MHz, CDCl$_3$): δ ppm 7.38-7.12 (m, 9H), 6.97-6.92 (m, 2H), 6.86-6.81 (m, 2H), 5.84 (d, J=10.1 Hz, 1H), 4.98 (d, J=6.0 Hz, 1H), 4.97 (d, J=10.5 Hz, 1H), 4.73 (d, J=11.8 Hz, 1H), 4.69 (d, J=11.8 Hz, 1H), 4.42 (d, J=10.1 Hz, 1H), 4.40 (d, J=10.5 Hz, 1H), 4.31 (br d, J=2.8 Hz, 1H), 4.26-4.20 (m, 2H), 3.93 (d, J=13.5 Hz, 1H), 3.78 (br s, 4H)

$^{13}$C-NMR (100 MHz, CDCl$_3$): δ ppm 206.7 (s, 1C), 155.5 (s, 1C), 150.8 (s, 1C), 137.1 (s, 1C), 136.9 (s, 1C), 135.5 (s, 1C), 129.4 (d, 1C), 129.2 (d, 1C), 128.5 (d, 2C), 128.2 (d, 1C), 128.0 (d, 1C), 127.9 (d, 2C), 127.8 (d, 1C), 118.2 (d, 2C), 114.6 (d, 2C), 102.8 (d, 1C), 84.4 (d, 1C), 82.7 (d, 1C), 80.6 (d, 1C), 74.5 (t, 1C), 72.5 (t, 1C), 71.9 (t, 1C), 69.6 (t, 1C), 55.6 (q, 1C)

HRMS-ESI (m/z): [M+Na]$^+$

Calcd for $C_{28}H_{28}NaO_7$, 499.1733; found 499.1737.

EXAMPLE 14

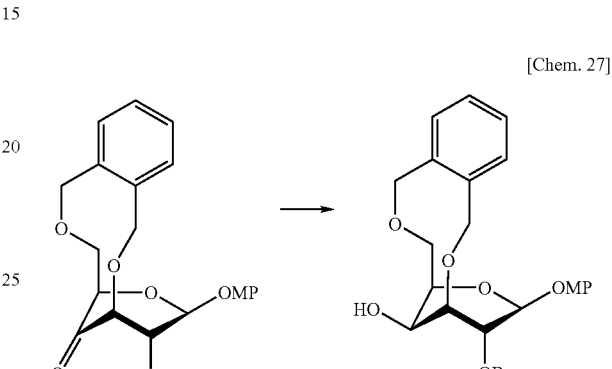

[Chem. 27]

Production of 4-methoxyphenyl 2-O-benzyl-3,6-O-(o-xylylene)-β-D-galactopyranoside A tetrahydrofuran (10 ml) solution of LiAlH(O-tert-$C_4H_9$)$_3$ (338 mg, 1.33 mmol) was added to a tetrahydrofuran (10 ml) solution of 4-methoxyphenyl 2-O-benzyl-3,6-O-(o-xylylene)-β-D-xylo-hexopyranoside-4-ulose (316 mg, 0.664 mmol) at room temperature under stirring. After stirring the mixture for another 45 minutes at the same temperature, water (10 ml) and 1M hydrochloric acid (10 ml) were subsequently added thereto. The mixture was extracted with ethyl acetate (20 ml×2). The combined organic layer was washed with saturated saline (10 ml×1), followed by drying over magnesium sulfate and filtration. The filtrate was concentrated, and the resulting residue was purified by flash column chromatography (silica gel 20 g, ethyl acetate/n-hexane=15/85→30/70) to afford 4-methoxyphenyl 2-O-benzyl-3,6-O-(o-xylylene)-β-D-galactopyranoside (312 mg, yield=98%) as a white powder.

The following are the physico-chemical properties of the object compound.

mp: 171° C. to 174° C.

$[\alpha]_D^{22}$=−22.0° (c=1.02, CHCl$_3$)

IR (ZnSe): 3455, 2870, 1509, 1219, 1152, 1088, 1044, 826, 758 cm$^{-1}$ $^1$H-NMR (400 MHz, CDCl$_3$): δ ppm 7.37-7.13 (m, 9H), 6.93-6.89 (m, 2H), 6.84-6.80 (m, 2H), 5.72 (d, J=9.4 Hz, 1H), 5.39 (d, J=12.1 Hz, 1H), 4.94 (d, J=5.3 Hz, 1H), 4.92 (d, J=12.1 Hz, 1H), 4.72 (d, J=11.9 Hz, 1H), 4.69 (d, J=11.9 Hz, 1H), 4.48-4.42 (m, 1H), 4.45 (d, J=9.4 Hz, 1H), 4.38 (ddd, J=8.2, 3.4, 1.6 Hz, 1H), 4.19 (dd, J=13.5 Hz, J=3.4 Hz, 1H), 4.06-3.98 (m, 3H), 3.86 (d, J=11.5 Hz, 1H), 3.78 (S, 3H)

$^{13}$C-NMR (100 MHz, CDCl$_3$): δ ppm 155.1 (s, 1C), 151.0 (s, 1C), 137.6 (s, 1C), 137.0 (s, 1C), 135.9 (s, 1C), 130.5 (s, 1C), 128.4 (d, 2C), 128.2 (d, 1C), 127.9 (d, 1C), 127.9 (d, 1C), 127.8 (d, 2C), 127.5 (d, 1C), 117.8 (d, 2C), 114.5 (d, 2C), 101.5 (d, 1C), 81.9 (d, 1C), 78.3 (d, 1C), 76.3 (d, 1C), 75.6 (t, 1C), 74.0 (t, 1C), 72.3 (t, 1C), 71.7 (d, 1C), 69.8 (t, 1C), 55.7 (q, 1C)

HRMS-ESI (m/z): [M+Na]$^+$

Calcd for $C_{28}H_{30}NaO_7$, 501.1889; found 501.1870.

EXAMPLE 15

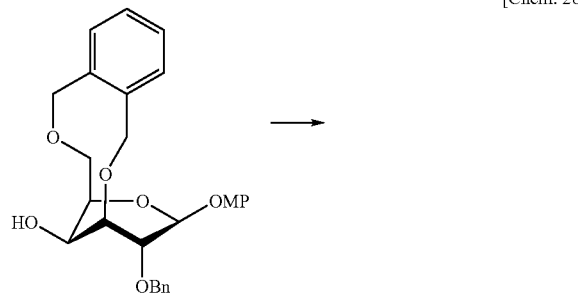

[Chem. 28]

Production of 4-methoxyphenyl 2,4-di-O-benzyl-3,6-O-(o-xylylene)-β-D-galactopyranoside A mixture of 4-methoxyphenyl 2-O-benzyl-3,6-O-(o-xylylene)-β-D-galactopyranoside (307 mg, 0.641 mmol), 60% NaH in mineral oil (76.8 mg, 46.1 mg as NaH, 1.92 mmol) and dimethylformamide (15 ml) was stirred, and benzyl bromide (219 mg, 1.28 mmol) was added thereto. The mixture was stirred for an hour at room temperature. Then, an aqueous saturated ammonium chloride solution (5.0 ml) was added to quench the reaction, and water (75 ml) was added. The mixture was extracted with ethyl acetate (50 ml×3). The combined ethyl acetate phase was successively washed with water (50 ml×1) and saturated saline (50 ml×1), followed by drying over magnesium sulfate and filtration. The filtrate was concentrated, and the resulting residue was purified by flash column chromatography (silica gel 10 g, ethyl acetate/n-hexane=5/95→20/80) to afford 4-methoxyphenyl 2,4-di-O-benzyl-3,6-O-(o-xylylene)-β-D-galactopyranoside (365 mg, quantitative yield) as a white amorphous solid.

The following are the physico-chemical properties of the object compound.

mp: 54° C. to 57° C.

$[\alpha]_D^{22}$=+4.30° (c=1.04, CHCl$_3$)

IR (ZnSe): 2869, 1507, 1455, 1215, 1169, 1094, 1048, 754, 735, 698 cm$^{-1}$ $^1$H-NMR (400 MHz, CDCl$_3$): δ ppm 7.38-7.26 (m, 10H), 7.19-7.12 (m, 4H), 6.92-6.87 (m, 2H), 6.81-6.78 (m, 2H), 5.99 (d, J=9.9 Hz, 1H), 5.71 (d, J=9.9 Hz, 1H), 4.90 (d, J=5.7 Hz, 1H), 4.76 (d, J=12.1 Hz, 1H), 4.67 (s, 2H), 4.60 (d, J=12.1 Hz, 1H), 4.47 (d, J=9.9 Hz, 1H), 4.44 (d, J=9.9 Hz, 1H), 4.30 (br d, J=8.9 Hz, 1H), 4.24 (dd, J=8.9 Hz, J=1.4 Hz, 1H), 4.16-4.09 (m, 1H), 4.07 (br s, 1H), 3.95-3.85 (m, 2H), 3.76 (s, 3H)

$^{13}$C-NMR (100 MHz, CDCl$_3$): δ ppm 155.0 (s, 1C), 151.1 (s, 1C), 137.8 (s, 1C), 137.8 (s, 1C), 137.7 (s, 1C), 137.3 (s, 1C), 128.9 (d, 1C), 128.5 (d, 1C), 128.4 (d, 2C), 128.3 (d, 2C), 127.7 (d, 2C), 127.6 (d, 2C), 127.4 (d, 2C), 127.3 (d, 1C), 127.2 (d, 1C), 117.8 (d, 2C), 114.3 (d, 2C), 101.5 (d, 1C), 82.9 (d, 1C), 77.8 (d, 1C), 76.9 (d, 1C), 74.3 (t, 1C), 74.0 (d, 1C), 72.7 (t, 1C), 72.3 (t, 1C), 72.1 (t, 1C), 67.4 (t, 1C), 55.5 (q, 1C)

HRMS-ESI (m/z): [M+Na]$^+$

Calcd for $C_{35}H_{36}NaO_7$, 591.2359; found 591.2344.

EXAMPLE 16

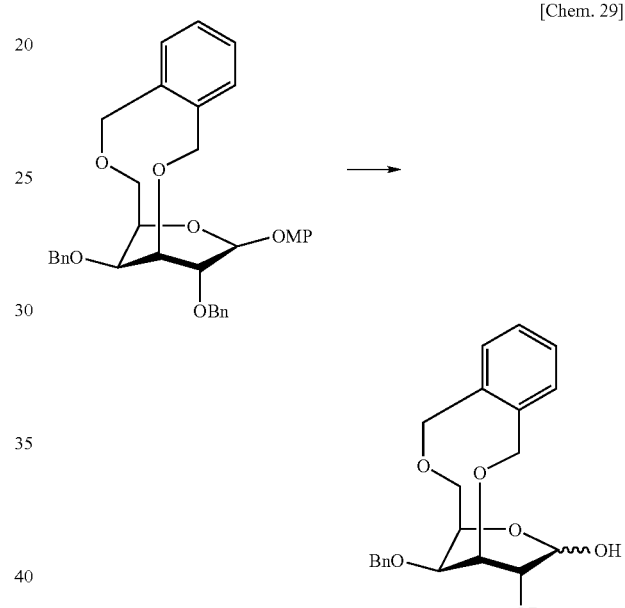

[Chem. 29]

Production of 2,4-di-O-benzyl-3,6-O-(o-xylylene)-D-galactopyranoside

Cerium(IV)sulfate (440 mg, 1.70 mmol) was added to a mixture of 4-methoxyphenyl 2,4-di-O-benzyl-3,6-O-(o-xylylene)-β-D-galactopyranoside (72.0 mg, 0.127 mmol), acetonitrile (5.0 ml) and water (1.0 ml) under stirring at room temperature. After stirring the resulting mixture for 12 hours at the same temperature, a 10% sodium thiosulfate aqueous solution (15 ml) was added to quench the reaction. The reaction mixture was extracted with ethyl acetate (20 ml×3). The organic phase was successively washed with water (20 ml×1) and saturated saline (20 ml×1), followed by drying over magnesium sulfate and filtration. The filtrate was concentrated, and the residue was purified by flash column chromatography (silica gel 10 g, ethyl acetate/n-hexane=5/95→40/60) to afford 2,4-di-O-benzyl-3,6-O-(o-xylylene)-D-galactopyranose (55.1 mg, yield=94%) as a white solid.

The following is the physico-chemical property of the object compound.

HRMS-ESI (m/z): [M+Na]$^+$

Calcd for $C_{28}H_{30}NaO_6$, 485.1940; found 485.1952.

EXAMPLE 17

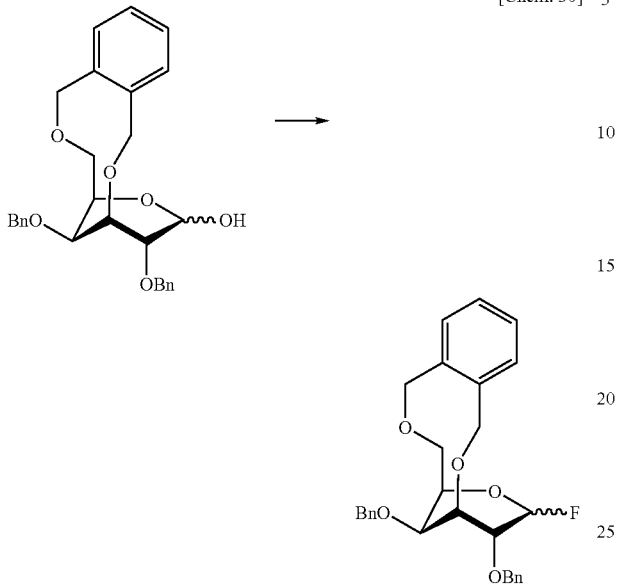

Production of 2,4-di-O-benzyl-3,6-O-(o-xylylene)-D-Galactopyranosyl Fluoride (Dimethylamino)sulfur trifluoride (144 mg, 0.896 mmol) was added to a tetrahydrofuran (9.0 ml) solution of 2,4-di-O-benzyl-3,6-O-(o-xylylene)-D-galactopyranose (207 mg, 0.448 mmol) under stirring. After the mixture was stirred for 45 minutes at room temperature, methanol (9.0 ml) was added, and the mixture was further stirred for 10 minutes at room temperature, followed by concentration. The resulting residue was purified by silica gel flash column chromatography (silica gel 20 g, ethyl acetate/n-hexane=5/95→30/70) to afford 2,4-di-O-benzyl-3,6-O-(o-xylylene)-D-galactopyranosyl fluoride (194 mg, yield=93%, anomer ratio=1/2.8) as colorless oil.

The following are the physico-chemical properties of the object compound.

Physico-chemical properties of major isomer;

$^1$H-NMR (400 MHz, acetone-$d_6$): δ ppm 7.43-7.17 (m, 14H), 5.84 (dd, J=53.4 Hz, J=3.4 Hz, 1H), 5.79 (d, J=9.4 Hz, 1H), 5.11 (d, J=9.6 Hz, 1H), 4.83 (d, J=11.9 Hz, 1H), 4.72 (d, J=11.9 Hz, 1H), 4.69 (d, J=11.9 Hz, 1H), 4.63 (d, J=11.9 Hz, 1H), 4.57 (d, J=9.4 Hz, 1H), 4.51-4.45 (m, 1H), 4.44 (d, J=9.6 Hz, 1H), 4.40-4.36 (m, 1H), 4.26-4.23 (m, 1H), 4.02 (dd, J=13.7 Hz, J=2.3 Hz, 1H), 3.89 (dd, J=13.7 Hz, J=1.6 Hz, 1H), 3.81 (ddd, J=15.6 Hz, J=3.4, 2.3 Hz, 1H)

$^{13}$C-NMR (100 MHz, acetone-$d_6$): δ ppm 140.2 (s, 1C), 140.0 (s, 1C), 139.9 (s, 2C), 130.8 (d, 1C), 130.4 (d, 1C), 129.9 (d, 2C), 129.9 (d, 2C), 129.3 (d, 1C), 129.3 (d, 2C), 129.2 (d, 2C), 129.1 (d, 2C), 129.0 (d, 1C), 106.1 (d, J=224.3 Hz, 1C), 79.5 (d, J=20.1 Hz, 1C), 77.9 (d, 1C), 76.3 (d, J=4.8 Hz, 1C), 75.3 (t, 1C), 74.0 (d, 1C), 73.5 (t, 1C), 73.4 (t, 1C), 73.0 (t, 1C), 70.0 (t, 1C)

HRMS-ESI (m/z): [M+Na]$^+$

Calcd for $C_{28}H_{29}FNaO_5$, 487.1897; found 487.1882.

Physico-chemical properties of minor isomer;

$^1$H-NMR (400 MHz, acetone-$d_6$): δ ppm 5.36 (dd, J=51.8 Hz, J=3.9 Hz, 1H), 3.71 (ddd, J=17.2 Hz, J=3.9, 1.6 Hz, 1H)

$^{13}$C-NMR (100 MHz, acetone-$d_6$): δ ppm 110.7 (d, J=215.7 Hz, 1C), 82.9 (d, J=29.7 Hz, 1C), 74.9 (d, J=4.8 Hz, 1C).

EXAMPLE 18

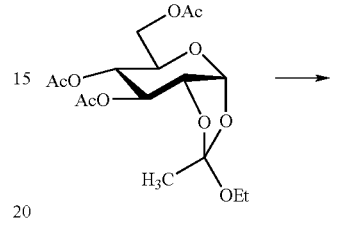

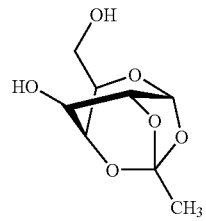

Production of 1,2,4-O-ethylidyne-α-D-glucopyranose 1,8-diazabicyclo[5.4.0]-7-undecene (405 mg, 2.66 mmol) was added to a methanol (20 ml) solution of 3,4,6-tri-O-acetyl-1,2-O-(1-ethoxyethylidene)-α-D-glucopyranose (1.0 g, 2.66 mmol). After stirring for 30 minutes at room temperature, the reaction mixture was concentrated. The residue was diluted with dichloroethane (28 ml), and 4 Å molecular sieve (710 mg) and p-toluene sulfonic acid monohydrate (19 mg, 99.9 μmol) were added to the solution. The obtained mixture was stirred under reflux for 6.5 hours. An aqueous sodium bicarbonate solution was added to quench the reaction, followed by filtration through Celite to remove the 4 Å molecular sieve. The filtrate was concentrated, and the resulting residue was purified by silica gel column chromatography (silica gel 10 g, ethyl acetate/n-hexane=1/2→ethyl acetate→ethyl acetate/methanol=50/1) to afford 1,2,4-O-ethylidyne-α-D-glucopyranose (449 mg, 22.0 mmol, yield=83%).

The NMR spectrum of the obtained compound coincided with the NMR spectrum of known 1,2,4-O-ethylidyne-alpha-D-glucopyranose.

EXAMPLE 19

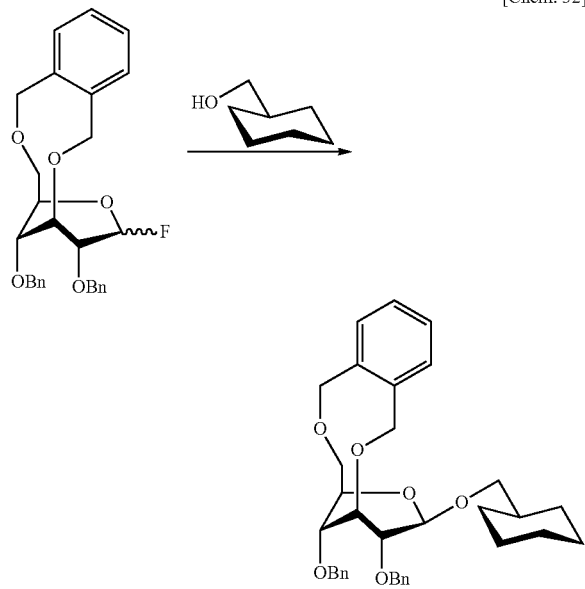

[Chem. 32]

β-O-glycosylation reaction

A mixture of a molecular sieve 5A (194 mg), $SnCl_2$ (2.4 mg, 1.3 mmol), $AgB(C_6F_5)_4$ (10.2 mg, 12.9 mmol) and benzotrifluoride (1.2 ml) was stirred, and cyclohexyl methanol (8.8 mg, 78 mmol) and the white powder (mixture of 2,4-di-O-benzyl-3,6-O-(o-xylylene)-D-glucopyranosyl fluoride (anomer mixture; anomer ratio=8/92))(30.0 mg, 64.6 mmol) obtained in Example 4 were successively added thereto. The mixture was stirred for 1.5 hours at room temperature, and an aqueous saturated sodium bicarbonate solution (5 ml) was added to quench the reaction, followed by filtration. The filtrate was extracted with ethyl acetate (30 ml).

The extract was washed with saturated saline, dried over sodium sulfate, filtrated, and concentrated.

The ratio of the α-isomer to the β-isomer in the obtained crude product was determined according to $^1$H-NMR (400 MHz, acetone-$d_6$). The crude product contained 99% or more β-isomers.

This crude product was purified by silica gel column chromatography (silica gel 2.0 g, n-hexane/diethylether=10/1→6/1) to afford cyclohexyl methyl 2,4-di-O-benzyl-3,6-O-(o-xylylene)-β-D-glucopyranoside (34.6 mg, yield=96%) as a colorless syrup.

The following are the physico-chemical properties of the obtained compound.

$[\alpha]_D^{25}$=+61.3° (c1.65, $CHCl_3$)

IR (ZnSe) 2922, 2853, 1117, 1030 cm$^{-1}$ $^1$H-NMR (400 MHz, $CDCl_3$): 7.40 (m, 10H), 7.21-7.09 (m, 4H), 5.57 (d, J=9.8 Hz, 1H), 5.08 (d, J=10.3 Hz, 1H), 4.78 (d, J=12.0 Hz, 1H), 4.68 (d, J=6.4 Hz, 1H), 4.67 (d, J=11.9 Hz, 1H), 4.51 (d, J=11.9 Hz, 1H), 4.39 (brdd, J=1.4, 1.4 Hz, 1H), 4.31 (d, J=10.3 Hz, 1H), 4.28 (d, J=9.8 Hz, 1H), 4.08 (brd, J=3.0 Hz, 1H), 3.92 (d, J=3.0 Hz, 1H), 3.81 (d, J=13.5 Hz, 1H), 3.75 (dd, J=13.5 Hz, 1H), 3.69 (dd, J=9.4, 6.1 Hz, 1H), 3.63 (dd, J=6.4, 0.9 Hz, 1H), 3.26 (dd, J=9.4, 7.1 Hz, 1H), 1.81 (brd, J=12.6 Hz, 1H), 1.75-1.55 (m, 5H), 1.28-1.09 (m, 3H), 0.96 (dd, J=12.1, 3.0 Hz, 1H), 0.90 (dd, J=11.5, 2.5 Hz, 1H)

$^{13}$C-NMR (100 MHz, $CDCl_3$): 139.0 (s, 1C), 138.2 (s, 1C), 137.3 (s, 1C), 136.7 (s, 1C), 129.7 (d, 1C), 128.7 (d, 1C), 128.6 (d, 2C), 128.4 (d, 2C), 128.0 (d, 3C), 127.9 (d, 2C), 127.8 (d, 2C), 127.6 (d, 1C), 102.9 (d, 1C), 83.3 (d, 1C), 82.6 (d, 1C), 75.6 (d, 1C), 75.3 (t, 1C), 74.9 (t, 1C), 72.8 (t, 1C), 72.0 (t, 1C), 70.7 (t, 1C), 70.5 (t, 1C), 70.5 (d, 1C), 38.2 (d, 1C), 30.3 (t, 1C), 30.1 (t, 1C), 26.8 (t, 1C), 26.1 (t, 1C), 26.0 (t, 1C)

HRMS-ESI (m/z): [M+Na]$^+$

Calcd for $C_{35}H_{42}NaO_6$, 581.2879; found 581.2873.

When toluene, diethylether or dichloromethane was used as a solvent instead of benzotrifluoride, β-O-glucopyranoside was obtained at almost the same yield.

EXAMPLE 20

β-O-glucopyranosides were produced in the same manner as in Example 19 using various alcohols shown in Table 1 instead of cyclohexyl methanol. The ratio of the α-isomer to the β-isomer in the obtained crude product was determined according to $^1$H-NMR (400 MHz, acetone-$d_6$). No α-isomer was detected in the crude product. Table 1 shows the yields of the obtained β-O-glucopyranosides.

TABLE 1

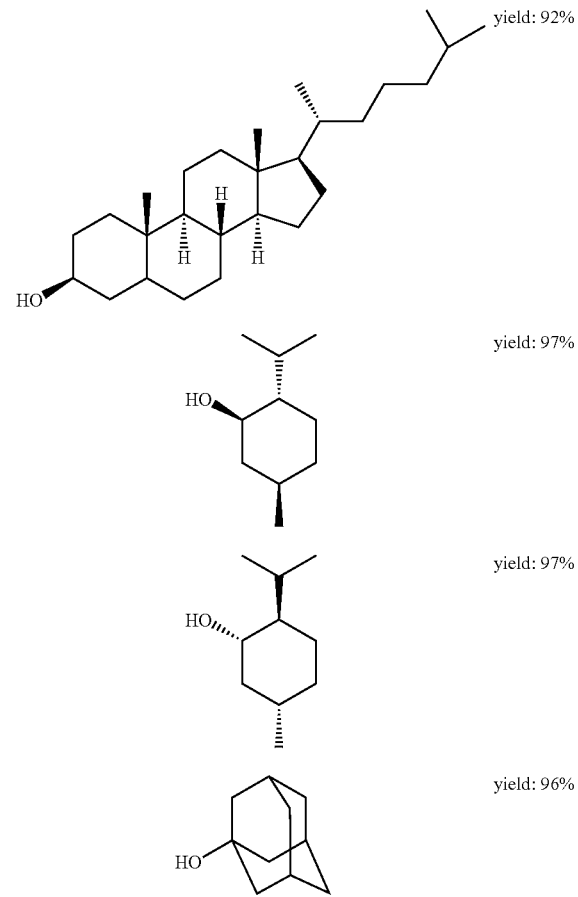

TABLE 1-continued

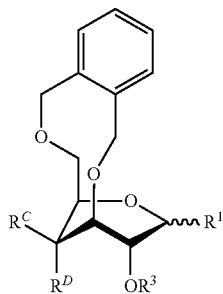

yield: 83% yield: 82%

The invention claimed is:

1. A 3,6-O-bridged pyranose-inverted compound, represented by the following formula:

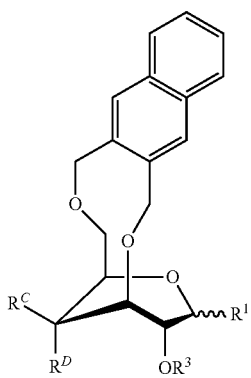

wherein one of $R^C$ and $R^D$ represents hydrogen and the other represents —$OR^2$; $R^1$ represents hydroxy or halogen; and $R^2$ and $R^3$ each represent a hydroxy-protecting group.

2. The 3,6-O-bridged pyranose-inverted compound according to claim 1, wherein $R^C$ represents hydrogen; and $R^D$ represents —$OR^2$.

3. The 3,6-O-bridged pyranose-inverted compound according to claim 1, wherein $R^C$ represents —$OR^2$; and $R^D$ represents hydrogen.

4. A 3,6-O-bridged pyranose-inverted compound, represented by the following formula:

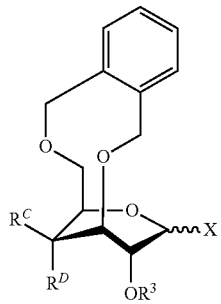

wherein one of $R^C$ and $R^D$ represents hydrogen and the other represents —$OR^2$; $R^1$ represents hydroxy or halogen; and $R^2$ and $R^3$ each represent a hydroxy-protecting group.

5. The 3,6-O-bridged pyranose-inverted compound according to claim 1, wherein the hydroxy-protecting group represented by $R^2$ and $R^3$ is benzyl, dimethyl benzyl, 4-methoxybenzyl, allyl or trialkyl silyl.

6. A process for producing β-O-pyranoside represented by the following formula:

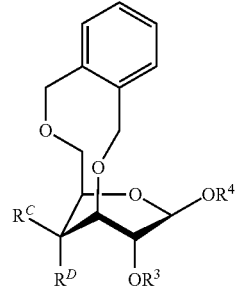

wherein one of $R^C$ and $R^D$ represents hydrogen and the other represents —$OR^2$; $R^2$ and $R^3$ each represent a hydroxy-protecting group; and $R^4$ represents a residue of a primary, secondary or tertiary alcohol, the process comprising reacting a 3,6-O-bridged pyranose-inverted compound represented by the following formula:

wherein X represents halogen; and $R^C$, $R^D$, $R^2$ and $R^3$ are the same as above, with an alcohol represented by $R^4OH$, wherein $R^4$ is the same as above.

7. The 3,6-O-bridged pyranose-inverted compound according to claim 4, wherein $R^C$ represents hydrogen; and $R^D$ represents —$OR^2$.

8. The 3,6-O-bridged pyranose-inverted compound according to claim 4, wherein $R^C$ represents —$OR^2$; and $R^D$ represents hydrogen.

9. The 3,6-O-bridged pyranose-inverted compound according to claim 4, wherein the hydroxy-protecting group represented by $R^2$ and $R^3$ is benzyl, dimethyl benzyl, 4-methoxybenzyl, allyl or trialkyl silyl.

10. A process for producing β-O-pyranoside represented by the following formula:

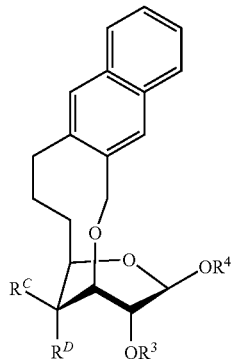

wherein one of $R^C$ and $R^D$ represents hydrogen and the other represents —$OR^2$; $R^2$ and $R^3$ each represent a hydroxy-protecting group; and $R^4$ represents a residue of a primary, secondary or tertiary alcohol, the process comprising reacting a 3,6-O-bridged pyranose-inverted compound represented by the following formula:

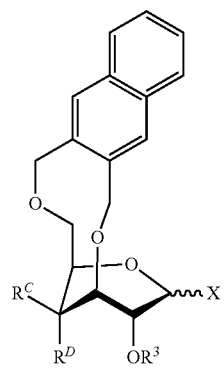

wherein X represents halogen; and $R^C$, $R^D$, $R^2$ and $R^3$ are the same as above, with an alcohol represented $R^4OH$, wherein $R^4$ is the same as above.

* * * * *